United States Patent
Pulaski et al.

(10) Patent No.: US 10,555,669 B2
(45) Date of Patent: Feb. 11, 2020

(54) OPTICAL COHERENCE TOMOGRAPHY SYSTEMS AND METHODS WITH DISPERSION COMPENSATION

(71) Applicant: AMO WAVEFRONT SCIENCES, LLC, Santa Ana, CA (US)

(72) Inventors: Paul D. Pulaski, Albuquerque, NM (US); Thomas D. Raymond, Edgewood, NM (US)

(73) Assignee: AMO Wavefront Sciences, LLC, Santa Ana, CA (US)

( * ) Notice: Subject to any disclaimer, the term of this patent is extended or adjusted under 35 U.S.C. 154(b) by 162 days.

(21) Appl. No.: 15/808,513

(22) Filed: Nov. 9, 2017

(65) Prior Publication Data

US 2018/0125354 A1 May 10, 2018

Related U.S. Application Data

(60) Provisional application No. 62/419,890, filed on Nov. 9, 2016.

(51) Int. Cl.
  *A61B 3/14* (2006.01)
  *A61B 3/10* (2006.01)

(52) U.S. Cl.
  CPC ............... *A61B 3/102* (2013.01); *A61B 3/14* (2013.01)

(58) Field of Classification Search
  CPC .......... A61B 3/102; A61B 5/0066; A61B 3/14
  USPC ................................ 351/206, 246, 212, 221
  See application file for complete search history.

(56) References Cited

U.S. PATENT DOCUMENTS

| | | | |
|---|---|---|---|
| 5,777,719 | A | 7/1998 | Williams et al. |
| 6,385,358 | B1 | 5/2002 | Everett et al. |
| 6,550,917 | B1 | 4/2003 | Neal et al. |
| 7,980,699 | B2 | 7/2011 | Neal et al. |
| 9,101,292 | B2 | 8/2015 | Zhou et al. |

(Continued)

FOREIGN PATENT DOCUMENTS

| | | |
|---|---|---|
| EP | 1919106 A1 | 5/2008 |
| EP | 2264841 B1 | 1/2016 |
| WO | 2015013651 A2 | 1/2015 |

OTHER PUBLICATIONS

Asaka K., et al., "Dispersion Matching of Sample and Reference Arms in Optical Frequency Domain Reflectometry-Optical Coherence Tomography Using a Dispersion-Shifted Fiber," Optics Express, Apr. 11, 2007, vol. 15 (8), pp. 5030-5042.

(Continued)

*Primary Examiner* — Hung X Dang
(74) *Attorney, Agent, or Firm* — Johnson & Johnson Surgical Vision, Inc.

(57) ABSTRACT

An optical coherence tomography (OCT) interferometer includes at least a first optical fiber of a first type having a first length, in series with a second optical fiber of a second type which is different than the first type and having a second length, in at least one of the sample path and/or the reference path of the OCT interferometer. The dispersion characteristics of the first optical fiber and the second optical fiber are significantly different than each other. As a result, the total group delay dispersion of a first portion of the laser light passing through the sample path and the total group delay dispersion of the second portion of the laser light passing through the reference path may offset each other at the detector.

17 Claims, 11 Drawing Sheets

(56) References Cited

U.S. PATENT DOCUMENTS

2011/0267340 A1* 11/2011 Kraus .................... A61B 3/102
345/419

OTHER PUBLICATIONS

International Search Report and Written Opinion for Application No. PCT/US2017/060929, dated Jan. 30, 2018, 12 pages.

Lankenau E., et al., "Dispersion Compensation for Proximal Scanning Rigid OCT Endoscopes," Proceedings Optical Diagnostics of Living Cells II, Jul. 1, 2004, vol. 5316, pp. 172-177.

Mejia-Barbosa Y., et al., "Object Surface for Applying a Modified Hartmann Test to Measure Corneal Topography," Applied Optics, Nov. 1, 2001, vol. 40 (31), pp. 5778-5786.

* cited by examiner

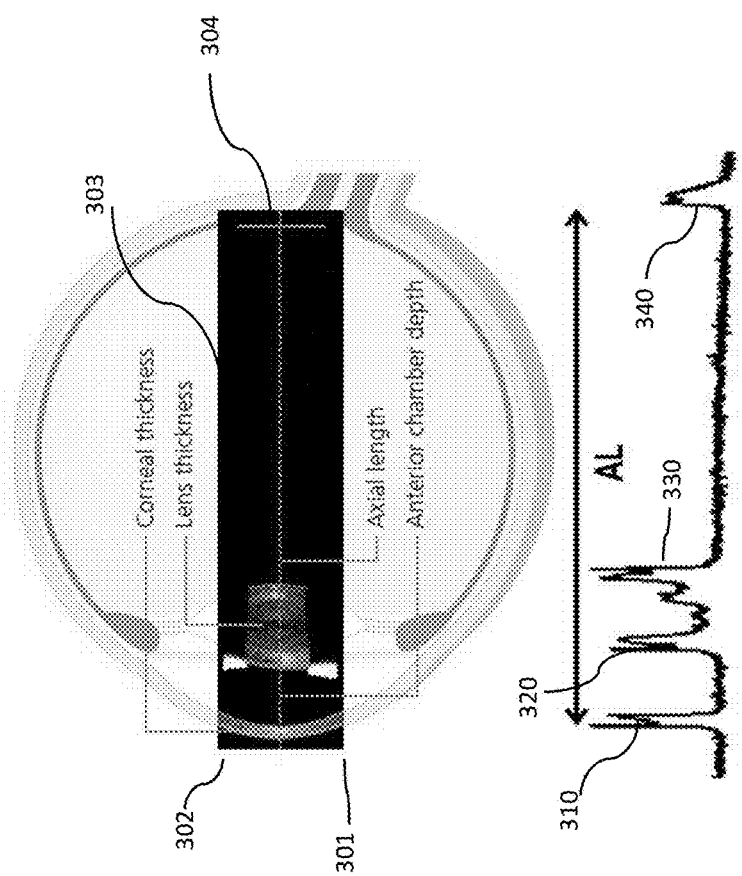
FIG. 8A
FIG. 8B
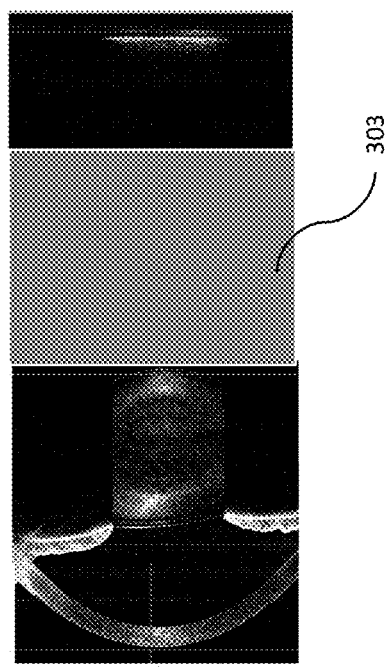
FIG. 8C

OPTICAL COHERENCE TOMOGRAPHY SYSTEMS AND METHODS WITH DISPERSION COMPENSATION

RELATED APPLICATIONS

This application claims priority to, and the benefit of, under U.S.C. § 119(e) of U.S. Provisional Appl. No. 62/419,890, filed on Nov. 9, 2016, which is incorporated herein by reference in its entirety.

TECHNICAL FIELD

Embodiments of this invention pertain to optical measurement systems and methods, and more particularly, to optical measurement systems and methods which employ optical coherence tomography (OCT) to characterize an eye.

BACKGROUND

Aberrometers measure the refraction of a subject's eye using infrared light.

Optical coherence tomography (OCT) is employed to measure the distances between different surfaces within an eye. Various types of OCT are known, including Fourier domain optical coherence tomography (FD-OCT), which in turn includes spectral domain optical coherence tomography (SD-OCT) and swept-source OCT (SS-OCT).

In SS-OCT, a swept (scanning) laser may be employed to produce a laser signal with a linear frequency ramp or "chirp." The swept laser signal is applied to a reference arm or reference path of an OCT interferometer, and also through a sample arm or sample path of the OCT interferometer to an object (e.g., an eye) which is to be measured. Reflections of the laser signal returned from the different surfaces of structures within the object (e.g., eye) in the sample path can be combined with the laser signal output by the reference path to produce corresponding OCT peaks, corresponding to the depths of the different reflection and scattering surfaces within the object being measured, in an OCT signal output by a detector.

The accuracy of the measurements depend on a number of factors, including the resolutions or "widths" of the peaks in the OCT signal produced by the different reflection and scattering surfaces within the object being measured. Meanwhile, the widths of the peaks in the OCT signal are affected by the total amount of group delay dispersion that is present due to the combination of the group velocity dispersion characteristics of the optical fibers and the optical system that comprise the OCT interferometer. In particular, any difference in group delay dispersion between the sample path and the reference path of the OCT interferometer can lead to significant broadening of the OCT peaks on the OCT output signal, which can affect the accuracy of the measurements.

It would therefore be desirable to reduce or minimize any difference in group delay dispersion differences between the sample arm and the reference arm of an OCT interferometer.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

FIG. 8A illustrates a preferred scanning region for the OCT subsystem according to many embodiments of the present invention.

FIG. 8B shows a representative graph of an intensity of an OCT signal of an OCT subsystem according to many embodiments as a function of depth along the axis defining the axial length of the eye.

FIG. 8C shows a cross-section of an eye obtained by an optical measurement system of the present invention using an OCT subsystem according to the present invention

DETAILED DESCRIPTION

Figure 1:
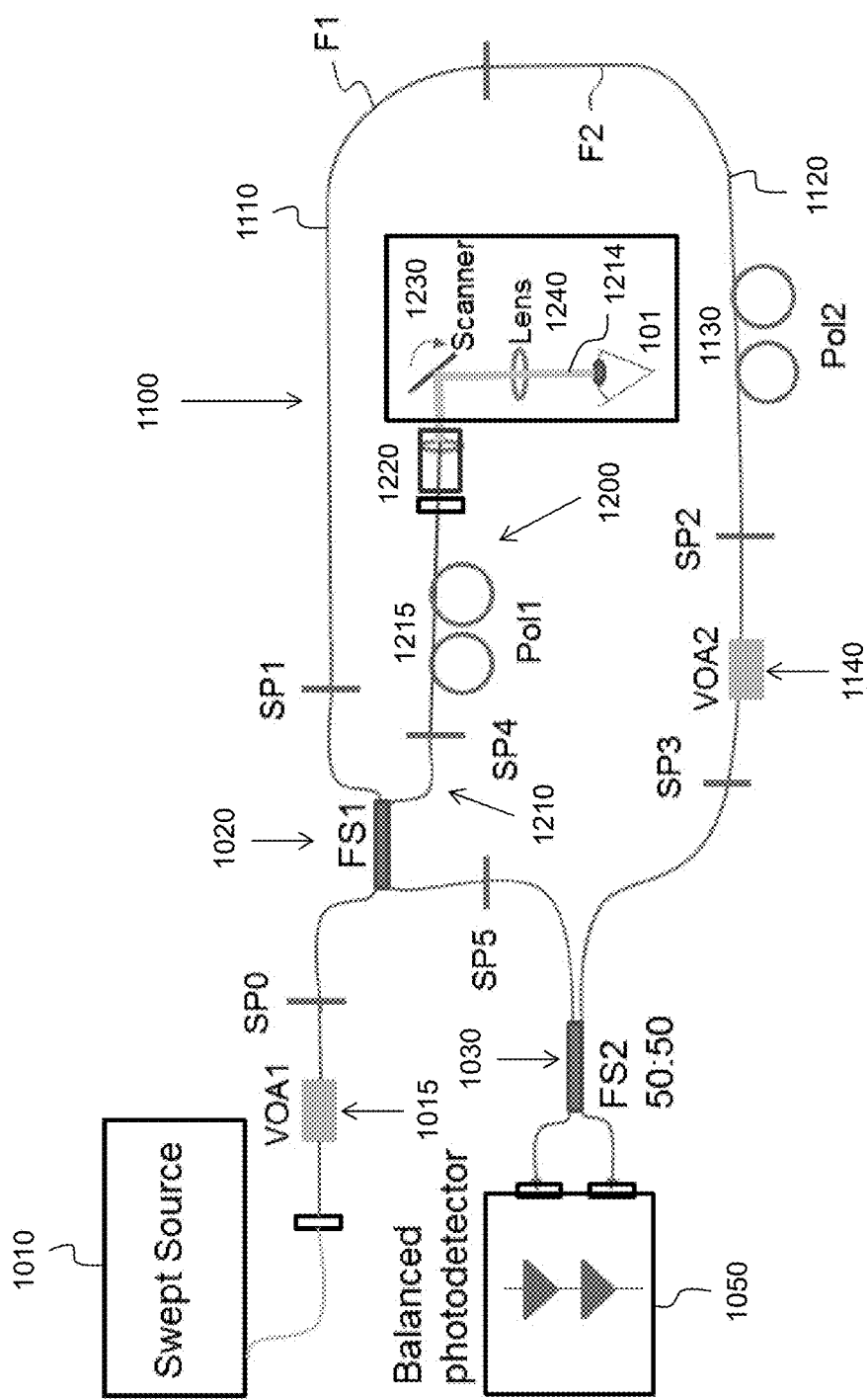
FIG. 1 illustrates an example embodiment of an optical coherence tomography (OCT) interferometer.

Exemplary embodiments of optical measurement systems and methods for measuring aberrations of an eye to illustrate various aspects and advantages of these devices and methods are described below. However, it should be understood that the principles involved in these devices and methods can be employed in a variety of other contexts, and therefore the novel devices and method disclosed and claimed here should not be construed as being limited to the example embodiments described below.

As described above, any difference in group delay dispersion between the sample arm and the reference arm of the OCT interferometer can lead to significant broadening of the OCT peaks in the OCT output signal, which can affect the accuracy of the depth measurements.

One technique which may be employed to compensate for the difference in group delay dispersion between the reference path and the sample path of an OCT interferometer is to match the optical material properties in the reference and sample paths. Because the sample path often includes a section of air, the reference path is often equipped with a comparable air path that requires the use of lenses, introducing additional cost and complexity. Often optical glass of a selected length is inserted in the air path of either the sample arm or the reference arm in the interferometer to match the group delay dispersions in the sample arm and the reference arm. To the extent that these procedures are not perfect, additional compensation may be achieved through the application of computer algorithms to the OCT output signal to minimize the effect due to the difference in the group delay dispersions between the two paths. Such an algorithm may be applied directly to the FFT in the OCT analysis.

However, due to the complexity and limitations of these techniques, there is a desire for other solutions.

Toward this end, the present inventors have determined that inserting two or more different optical fibers which have different group velocity dispersion constants than each other in series in the reference arm of the OCT interferometer, and by choosing an appropriate combination of different fibers with different group velocity dispersion constants, and appropriate lengths for the different optical fibers, the different group velocity dispersion constants can be balanced so as to minimize or eliminate the group delay dispersion difference between the reference path and the sample path and to cancel out the effect of such group delay dispersion differences.

A principal advantage of this solution is that it can directly compensate for the group delay dispersion differences within the fiber interferometer without the need for an air section in the reference path. This feature eliminates the costs associated with the lenses, support structure and alignment time, while increasing the system robustness against misalignment. In contrast, the computer algorithms mentioned above may not be able to effectively compensate for the group delay dispersion difference, and the insertion of the optical glass may be too cumbersome (due to the required length) and could lead to unacceptable signal loss, especially if the glass has to be inserted in the sample path.

FIG. 1 illustrates an example embodiment of an optical coherence interferometry (OCT) interferometer 1000 which may be employed for swept-source OCT (SS-OCT) and which may employ one or more principles described above.

OCT interferometer 1000 includes a swept laser light source 1010, a variable optical attenuator (VOA) 1015, a first fiber splitter 1020, a reference path 1100, a sampling path 1200, a second fiber splitter 1030, and a detector 1050.

Reference path 1100 includes a first optical fiber 1110, a second optical fiber 1120, a first polarizer 1130, and a second VOA 1140. Beneficially, reference path 1100 has a defined optical path length.

Beneficially, first optical fiber 1110 and second optical fiber 1120 which are connected in series with each other have different group velocity dispersion characteristics from each other. In particular, the differences in the group velocity dispersion characteristics between first optical fiber 1110 and second optical fiber 1120 are substantially greater than any group velocity dispersion characteristic differences between two optical fibers of the same type and/or part number which may result from manufacturing variations or specified tolerances.

In some embodiments, first optical fiber 1110 and second optical fiber 1120 may have group velocity dispersion constants for at least one frequency within the swept bandwidth of swept laser light source 1010 which are different than each other by at least one percent. We define this situation herein as first optical fiber 1110 and second optical fiber 1120 having significantly different dispersion characteristics than each other.

In some embodiments, first optical fiber 1110 and second optical fiber 1120 may have group velocity dispersion constants for at least one frequency within the swept bandwidth of swept laser light source 1010 which are different than each other by at least ten percent. We define this situation herein as first optical fiber 1110 and second optical fiber 1120 having substantially different dispersion characteristics than each other.

In some embodiments, first optical fiber 1110 and second optical fiber 1120 may have different material properties, core diameters, cladding layer outside diameters, and/or coating layer outside diameters than each other. For example, in various embodiments, first optical fiber 1110 and second optical fiber 1120 may have different mode field diameters, maximum attenuations, core refractive indices, and/or numerical apertures than each other.

In some embodiments, one of first and second optical fibers 1110 and 1120 may comprise an HI-1060 type optical fiber, manufactured by CORNING®, and the other of first and second optical fibers 1110 and 1120 may comprise an SM-980 type optical fiber, manufactured by NEWPORT®. However, other optical fibers may be employed in place of one or both of these examples, so long as the dispersion characteristics of the two optical fibers are significantly different than each other within the swept bandwidth of swept laser light source 1010.

Sampling path 1200 includes an optical fiber 1210, a polarizer 1215, a Z-scan device 1220, a scanner 1230, and one or more optical lenses 1240, and delivers a probe beam 1214 into an eye 101 under test. Z-scan device 1220 may comprise a Z-telescope which may be controlled by a controller (not shown in FIG. 1) to focus probe beam 1214 at a desired depth within eye 101. Scanner 1230 scans the probe beam in X and Y directions to span an X-Y OCT measurement space in eye 101. In some embodiments, scanner 1230 may comprise an X-Y scanner. In other embodiments, scanner 1230 may comprise a separate X-scanner and a separate Y-scanner.

In some embodiments, probe beam 1214 passes through a significant length of air in sampling path 1200 in travelling to and from eye 101. Accordingly, the total group delay dispersion which is applied to probe beam 1214 through sampling path 1200 depends not only on the dispersion characteristics of fiber 1210, but also the dispersion characteristics of the air, the relative lengths of the optical paths through optical fiber 1210 and the air, the dispersion characteristics of one or more optical lenses 1240, etc.

The optical fibers 1110 and 1120 having different group velocity dispersion coefficients that each other can be employed to balance or offset the group delay dispersion characteristics of sampling path 1200 by selecting corresponding lengths for optical fibers 1110 and 1120 to improve the resolution of the OCT peaks in the OCT signal detected by detector 1050. Given the group delay dispersion characteristics of sampling path 1200, and the group velocity dispersion characteristics of optical fibers 1110 and 1120, the appropriate lengths for optical fibers 1110 and 1120 can be determined theoretically, empirically, or by a combination of both.

Beneficially, detector 1050 may comprise a balanced photodiode detector.

In operation, the wavelengths for swept laser light source 1010 can be centered at wavelengths from 840 nm to 1310 nm. As a non-limiting example, OCT interferometer 1000 may be configured to employ a swept source having wavelengths of around 1060 nm with an 8 mm scan depth. The spatial disposition of the eye structures using optical coherence tomography should generally be measured while the patient is engaged with a patient interface, as described below. The OCT scan depth may be between 8 and 50 mm, and the scan depth may be greater than about 24 mm or even 30 mm to achieve a full scan depth for eye 101.

Sample path 1200 is configured to receive a first portion of the laser light from swept laser light source 1010 via first fiber splitter 1020, to direct the first portion of the laser light to eye 101 as a probe beam 1214, and to receive a returned portion of the probe beam from eye 101, returned by reflection and/or scattering and to direct the returned portion of probe beam 1214 to detector 1050 via second fiber splitter 1030.

Reference path 1100 is configured to receive a second portion of the laser light from swept laser light source 1010 via first fiber splitter 1020, and to pass the second portion of the laser signal therethrough to detector 1050 via second fiber splitter 1030.

Detector 1050 is configured to receive the returned portion of the probe beam from eye 101, returned by reflection and/or scattering, and to also receive the second portion of the laser light from swept laser light source 1010 which passed through reference path 1100, and in response thereto to output an OCT signal having optical peaks whose relative timing representing the depths of various reflection and scattering surfaces within eye 101. Beneficially, detector 1050 may comprise a balanced photodiode detector which generates and outputs an OCT signal based on an interference pattern between the returned portion of the probe beam from eye 101, returned by at least one reflection and scattering, and the second portion of the laser light from swept laser light source 1010 which passed through reference path 1100.

Further details about the operating principles of an OCT interferometer for SS-OCT are known and a description thereof will not be repeated here for brevity.

Although OCT interferometer 1000 employs two optical fibers 1110 and 1120 having significantly different dispersion characteristics than each other, connected in series with each other, in other embodiments three or more optical fibers having significantly different dispersion characteristics than each other may be connected in series with each other in reference path 1100. Furthermore, in other embodiments it is possible that two or more optical fibers having significantly different dispersion characteristics than each other may be connected in series with each other in sampling path 1200 in addition to, or in place of, having two optical fibers 1110 and 1120 in series with each other in reference path 1100.

Figure 2:
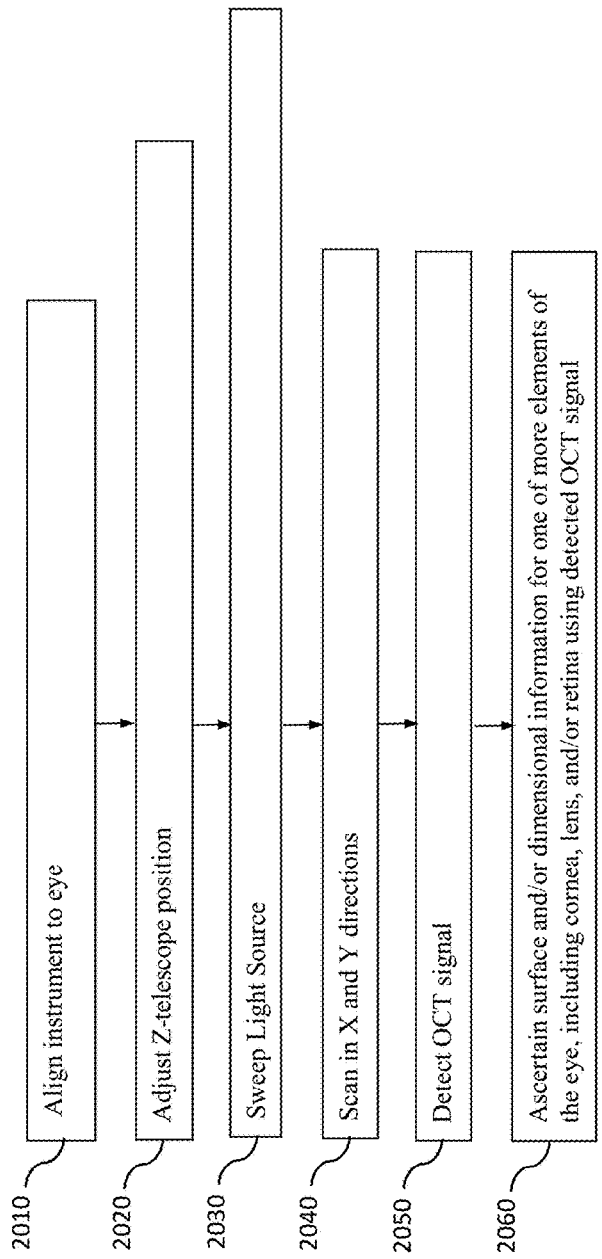
FIG. 2 is a flowchart of an example embodiment of a method of measuring one or more characteristics of an eye with an OCT interferometer.

FIG. 2 is a flowchart of an example embodiment of a method 2000 of measuring one or more characteristics of an eye with an OCT interferometer such as OCT interferometer 1000.

An operation 2010 includes aligning the measurement instrument, including the OCT interferometer, to the eye to be measured.

An operation 2020 includes adjusting a Z-axis telescope of the OCT interferometer to focus the probe beam at a desired depth within the eye.

An operation 2030 includes sweeping a frequency of a laser light source of the OCT interferometer across a desired frequency range with a linear frequency ramp or "chirp."

An operation 2040 includes scanning the probe beam in X and Y directions to span an X-Y OCT measurement space in the eye.

An operation 2050 includes detecting light from the reference path and the returned light from the eye, returned by reflection and/or scattering, to produce an OCT signal for a variety of points in the X-Y measurement space in the eye while the probe beam is scanned in the X and Y directions.

An operation 2060 includes ascertaining surface and/or dimensional information for one of more elements of the eye, including for example the cornea, lens, and/or retina, using peaks in the OCT output signal.

The principles of OCT interferometer 1000, as described above, may be applied to an optical measurement instrument which includes additional functionality, such as the ability to measure corneal topography and/or to make wavefront aberrometry measurements for they eye. Embodiments of such an optical measurement instrument, and methods of operation thereof, will now be described.

Figure 3C:
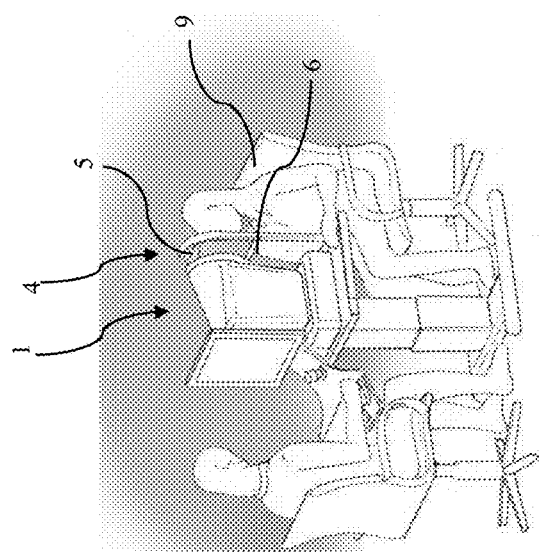
FIG. 3C illustrates a side perspective view showing an optical measurement system according to many embodiments.
Figure 3A:
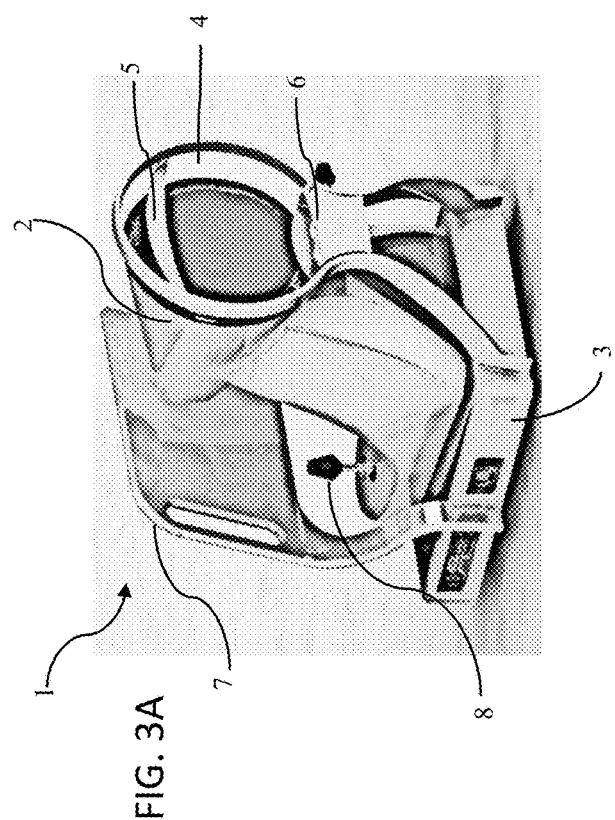
FIG. 3A illustrates a front perspective view showing an optical measurement system according to many embodiments.
Figure 3B:
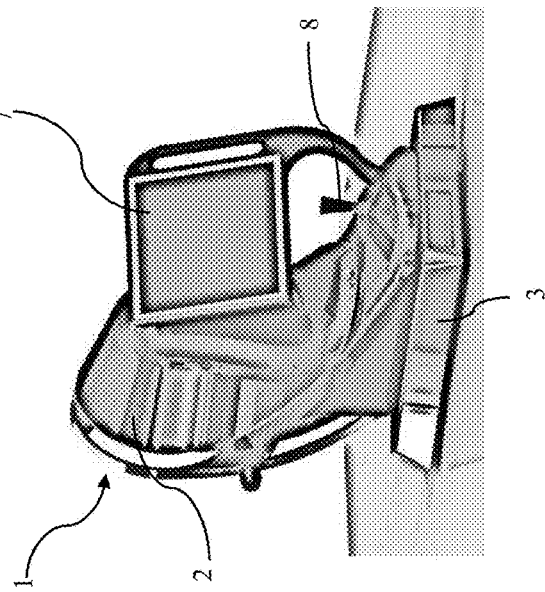
FIG. 3B illustrates a rear perspective view showing an optical measurement system according to many embodiments.

As shown in FIGS. 3A-3C, an optical measurement system 1, according to many embodiments, is operable to provide for a plurality of measurements of the human eye, including wavefront aberrometry measurements, corneal topography measurements, and optical coherence tomography measurements to measure characteristics of the cornea, the lens capsule, the lens and the retina. Optical measurement system 1 includes a main unit 2 which comprises a base 3 and includes many primary subsystems of many embodiments of optical measurement system 1. For example, externally visible subsystems include a touch-screen display control panel 7, a patient interface 4 and a joystick 8.

Patient interface 4 may include one or more structures configured to hold a patient's head in a stable, immobile and comfortable position during the diagnostic measurements while also maintaining the eye of the patient in a suitable alignment with the diagnostic system. In a particularly preferred embodiment, the eye of the patient remains in substantially the same position relative to the diagnostic system for all diagnostic and imaging measurements performed by optical measurement system 1.

In one embodiment patient interface 4 includes a chin support 6 and/or a forehead rest 5 configured to hold the head of the patient in a single, uniform position suitably aligned with respect to optical measurement system 1 throughout the diagnostic measurement. As shown in FIG. 3C, the optical measurement system 1 may be disposed so that the patient may be seated in a patient chair 9. Patient chair 9 can be configured to be adjusted and oriented in three axes (x, y, and z) so that the patent's head can be at a suitable height and lateral position for placement on the patient interface.

In many embodiments, optical measurement system 1 may include external communication connections. For example, optical measurement system 1 can include a network connection (e.g., an RJ45 network connection) for connecting optical measurement system 1 to a network. The network connection can be used to enable network printing of diagnostic reports, remote access to view patient diagnostic reports, and remote access to perform system diagnostics. Optical measurement system 1 can include a video output port (e.g., HDMI) that can be used to output video of diagnostic measurements performed by optical measurement system 1. The output video can be displayed on an external monitor for, for example, viewing by physicians or users. The output video can also be recorded for, for example, archival purposes. Optical measurement system 1 can include one or more data output ports (e.g., USB) to enable export of patient diagnostic reports to, for example, a data storage device or a computer readable medium, for example a non-volatile computer readable medium, coupled to a laser cataract surgery device for use of the diagnostic measurements in conducting laser cataract surgeries. The diagnostic reports stored on the data storage device or computer readable medium can then be accessed at a later time for any suitable purpose such as, for example, printing from an external computer in the case where the user without access to network based printing or for use during cataract surgery, including laser cataract surgery.

Figure 4:
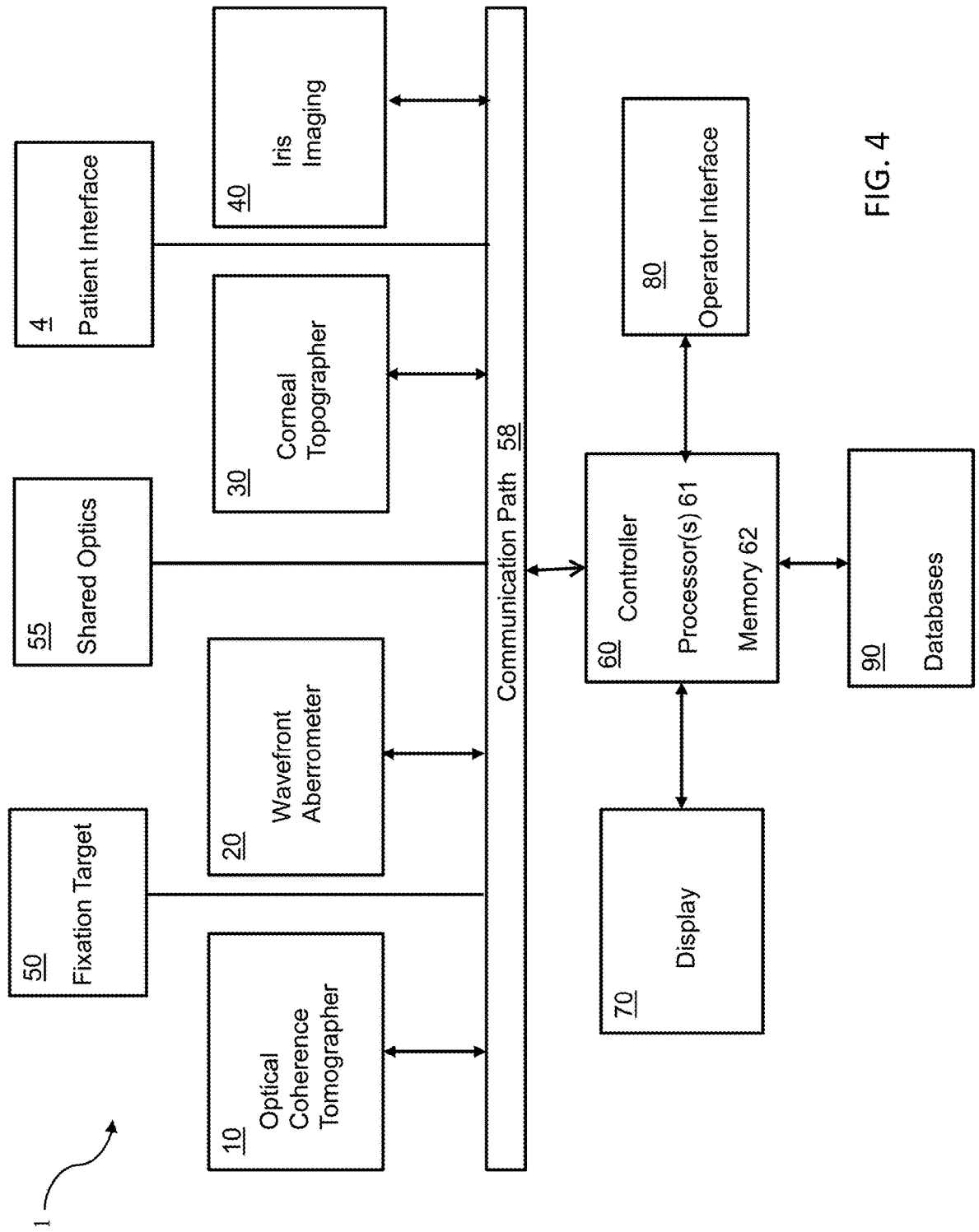
FIG. 4 is a block diagram of a system including an optical measurement instrument, and a position of an eye relative to the system according to one or more embodiments described herein which may be used by the optical measurement.

FIG. 4 is a block diagram of optical measurement system 1 according to one or more embodiments described herein. Optical measurement system 1 includes: an optical coherence tomography (OCT) subsystem 10, a wavefront aberrometer subsystem 20, and a corneal topographer subsystem 30 for measuring one or more characteristics of a subject's eye. Optical measurement system 1 may further include an iris imaging subsystem 40, a fixation target subsystem 50, a controller 60, including one or more processor(s) 61 and memory 62, a display 70 and an operator interface 80. Optical measurement system 1 further includes patient interface 4 for a subject to present his or her eye for measurement by optical measurement system 1.

Optical coherence tomography subsystem 10 is configured to measure the spatial disposition (e.g., three-dimensional coordinates such as X, Y, and Z of points on boundaries) of eye structures in three dimensions. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, the limbus and/or the retina. The spatial disposition of the structures of interest and/or of suitable matching geometric modeling such as surfaces and curves can be generated and/or used by controller 60 for a number of purposes, including, in some embodiment to program and control a subsequent laser-assisted surgical procedure. The spatial disposition of the structures of interest and/or of suitable matching geometric modeling can also be used to determine a wide variety of parameters. Beneficially, optical coherence tomography subsystem 10 may employ swept source optical coherence tomography (SS-OCT) as described above. Beneficially, optical coherence tomography subsystem 10 may comprise OCT interferometer 1000.

Wavefront aberrometer subsystem 20 is configured to measure ocular aberrations, which may include low and high order aberrations, by measuring the wavefront emerging from the eye by, for example a Shack Hartman sensor.

Corneal topographer subsystem 30 may apply any number of modalities to measure the shape of the cornea including one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Hartmann-Shack measurement of the eye, a Scheimpflug image topography of the eye, a confocal tomography of the eye, a Helmholtz source topographer, or a low coherence reflectometry of the eye. The shape of the cornea should generally be measured while the patient is engaged with patient interface 4.

Fixation target system 50 is configured to control the patient's accommodation, because it is often desired to measure the refraction and wavefront aberrations when an eye under measurement is focused at its far point Images captured by corneal topographer subsystem 10, wavefront aberrometer 20, optical coherence tomographer subsystem 30 or camera 40 may be displayed with a display of operator interface 80 or display 70 of optical measurement system 1, respectively. Operator interface 80 may also be used to modify, distort, or transform any of the displayed images.

Shared optics 55 provide a common propagation path that is disposed between patient interface 4 and each of optical coherence tomography (OCT) subsystem 10, wavefront aberrometer subsystem 20, corneal topographer subsystem 30, and in some embodiments, camera 40, and fixation target 50. In many embodiments, shared optics 55 may comprise a number of optical elements, including mirrors, lenses and beam combiners to receive the emission from the respective subsystem to the patient's eye and, in some cases, to redirect the emission from a patient's eye along the common propagation path to an appropriate director.

Controller 60 controls the operation of optical measurement system 1 and can receive input from any of optical coherence tomographer (OCT) subsystem 10, wavefront aberrometer subsystem 20, corneal topographer subsystem 30 for measuring one or more characteristics of a subject's eye, camera 40, fixation target 50, display 70 and operator interface 80 via communication paths 58. Controller 60 can include any suitable components, such as one or more processor, one or more field-programmable gate array (FPGA), and one or more memory storage devices. In many embodiments, controller 60 controls display 70 to provide for user control over the laser eye surgery procedure for pre-cataract procedure planning according to user specified treatment parameters as well as to provide user control over the laser eye surgery procedure. Communication paths 58 can be implemented in any suitable configuration, including any suitable shared or dedicated communication paths between controller 60 and the respective system components.

Operator interface 80 can include any suitable user input device suitable to provide user input to controller 60. For example, user interface devices 80 can include devices such as joystick 8, a keyboard, or a touchscreen display.

Figure 5A:
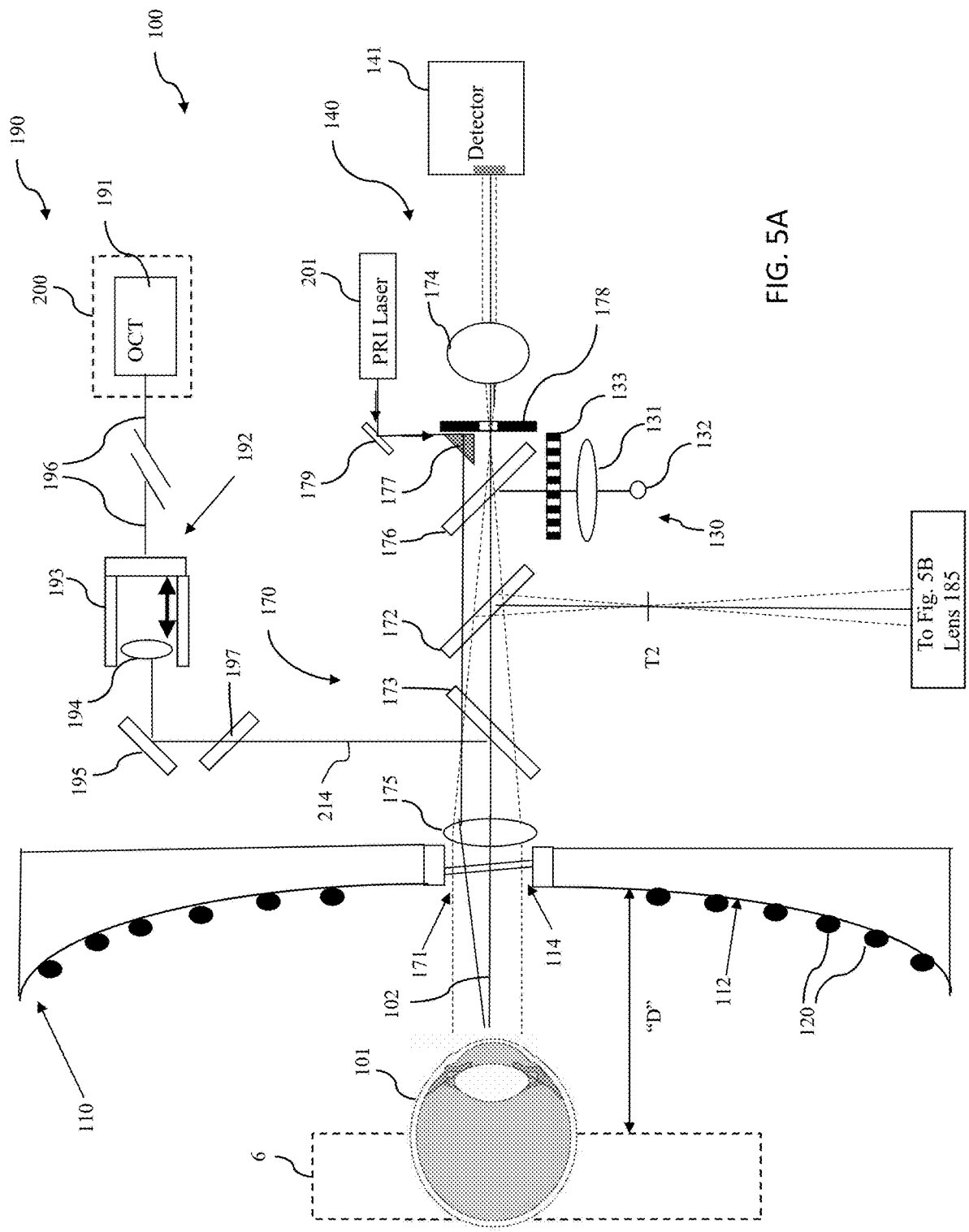
FIGS. 5A and 5B illustrate together an assembly illustrating a suitable configuration and integration of an optical coherence tomographer subsystem, a wavefront aberrometer subsystem a corneal topographer subsystem, an iris imaging subsystem, a fixation target subsystem according to a non-limiting embodiment of the present invention.
Figure 5B:
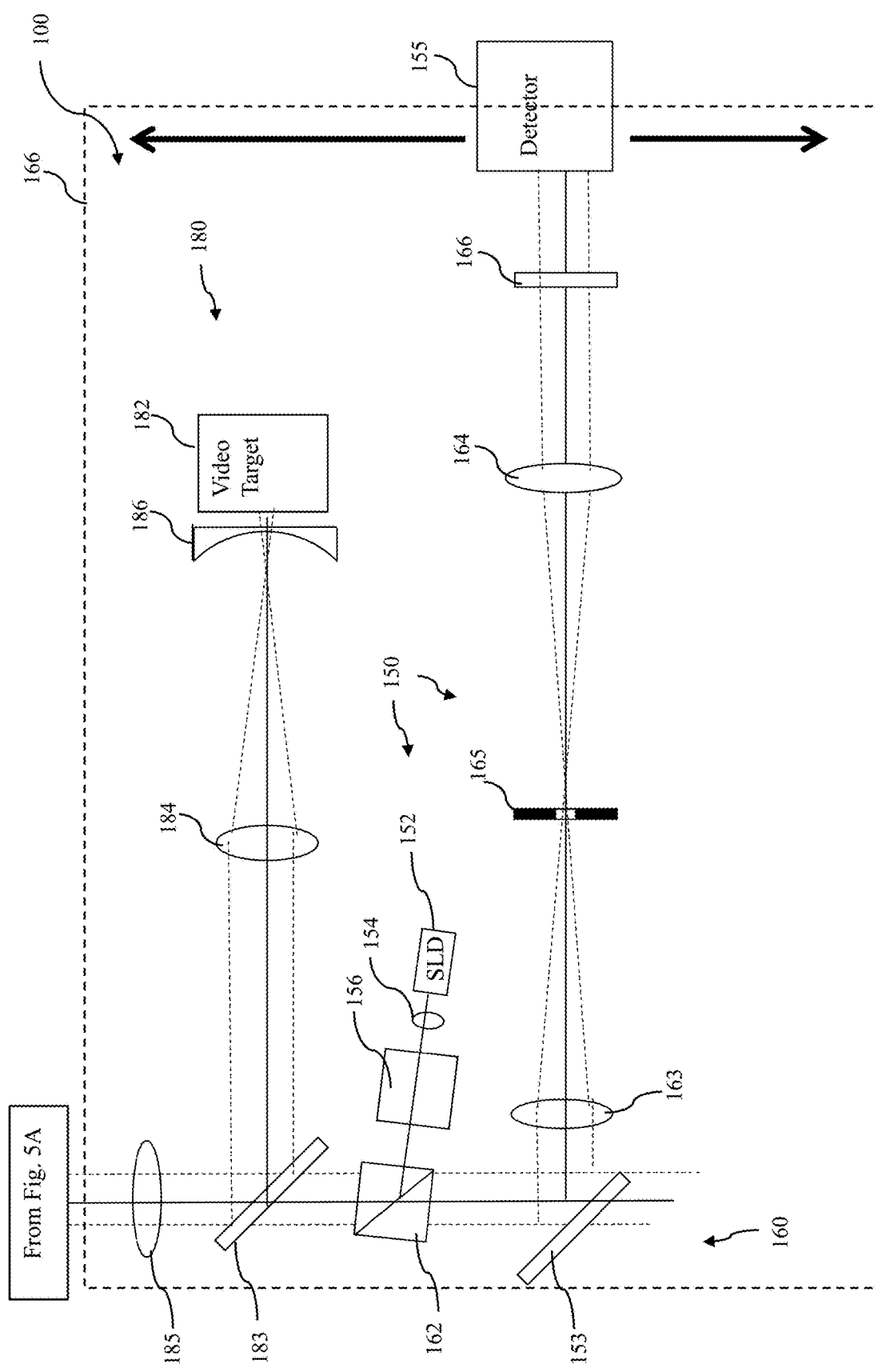

FIGS. 5A and 5B are simplified block diagrams illustrating an assembly 100 according to many embodiments which may be included in optical measurement system 1. Assembly 100 is a non-limiting example of suitable configurations and integration of an optical coherence tomography (OCT) subsystem 190, a wavefront aberrometer subsystem 150, a corneal topographer subsystem 140 for measuring one or more characteristics of a subject's eye, camera 40, a fixation target subsystem 180 and shared optics.

The shared optics generally comprise one or more components of a first optical system 170 disposed along a central axis 102 passing through the opening or aperture 114 of the structure 110. First optical system 170 directs light from the various light sources along the central axis 102 towards an eye 101 and establishes a shared or common optical path along which the light from the various light sources travel to eye 101. In one embodiment, optical system 170 comprises a quarter wave plate 171, a first beamsplitter 172, a second beamsplitter 173, an optical element (e.g., a lens) 174, a second lens 175, a third beamsplitter 176, and a structure including an aperture 178. Additional optical systems may be used in assembly 100 to direct light beams from one or more light sources to the first optical system 170. For example, a second optical system 160 directs light to the first optical system 170 from wavefront aberrometer subsystem 150 and comprises mirror 153, beam splitter 183 and lens 185.

Other configurations of assembly 100 may be possible and may be apparent to a person of skill in the art.

Corneal topographer subsystem 140 comprises a structure 110 having a principal surface 112 with an opening or aperture 114 therein; a plurality of first (or peripheral) light sources 120 provided on the principal surface 112 of structure 110; a Helmholz light source 130; and a detector, photodetector, or detector array 141.

In one embodiment, structure 110 has the shape of an elongated oval or "zeppelin" with openings or apertures at either end thereof. An example of such a structure is disclosed in Yobani Meji'a-Barbosa et al., "Object surface for applying a modified Hartmann test to measure corneal topography," APPLIED OPTICS, Vol. 40, No. 31 (Nov. 1, 2001) ("Meji'a-Barbosa"). In some embodiments, principal surface 112 of structure 110 is concave when viewed from the cornea of eye 101, as illustrated in FIG. 5A.

In one embodiment where principal surface 112 is concave, principal surface 112 has the shape of a conical frustum. Alternatively, principal surface 112 may have a shape of hemisphere or some other portion of a sphere, with an opening or aperture therein. Also alternatively, principal surface 112 may have the shape of a modified sphere or conical frustum, with a side portion removed. Beneficially, such an arrangement may improve the ergonomics of assembly 100 by more easily allowing structure 110 to be more closely located to a subject's eye 1001 without being obstructed by the subject's nose. Of course, a variety of other configurations and shapes for principal surface 112 are possible.

In the embodiment of FIG. 5A, the plurality of first light sources 120 are provided on the principal surface 112 of structure 110 so as to illuminate the cornea of eye 101. In one embodiment, light sources 122 may comprise individual light generating elements or lamps, such as light emitting diodes (LEDs) and/or the tips of the individual optical fibers of a fiber bundle. Alternatively, principal surface 112 of structure 110 may have a plurality of holes or apertures therein, and one or more backlight lamps, which may include reflectors and/or diffusers, may be provided for passing lighting through the holes to form the plurality of first light sources 120 which project light onto the cornea of eye 101. Other arrangements are possible.

In another embodiment, structure 110 is omitted from assembly 100, and the first light sources 120 may be independently suspended (e.g., as separate optical fibers) to form a group of first light sources 120 arranged around a central axis, the group being separated from the axis by a radial distance defining an aperture in the group (corresponding generally to the aperture 114 in the structure 110 illustrated in FIG. 5A).

In operation, a ray (solid line) from one of the first light sources 120 is reflected by the cornea and passes through optical system 170 (including aperture 178) to appear as a light spot on detector array 141. It will be appreciated that this ray is representative of a small bundle of rays that make it through optical system 170 and onto detector array 141, all of which will focus to substantially the same location on detector array 141. Other rays from that first light source 120 are either blocked by the aperture 178 or are otherwise scattered so as to not pass through the optical system 170. In similar fashion, light from the other first light sources 120 are imaged onto detector array 141 such that each one of first light sources 120 is imaged or mapped to a location on detector array 141 that may be correlated to a particular reflection location on the cornea of eye 101 and/or the shape of the cornea. Thus, detector array 141 detects the light spots projected thereon and provides corresponding output signals to a processor of controller 60 (FIG. 4). The processor determines the locations and/or shape of the light spots on detector array 141, and compares these locations and/or shapes to those expected for a standard or model cornea, thereby allowing the processor of controller 60 to determine the corneal topography. Alternatively, other ways of processing the spot images on detector array 141 may be used to determine the corneal topography of eye 101, or other information related to the characterization of eye 101.

Detector array 141 comprises a plurality of light detecting elements arranged in a two dimensional array. In one embodiment, detector array 141 comprises such a charge-coupled device (CCD), such as may be found in a video camera. However, other arrangements such as a CMOS array, or another electronic photosensitive device, may be employed instead. Beneficially, the video output signal(s) of detector array 141 are provided to processor 60 which processes these output signals as described in greater detail below.

Assembly 100 also comprises a Helmholtz light source 130 configured according to the Helmholtz principle. As used herein, the term "Helmholtz source" or "Helmholtz light source" means one or a plurality of individual light sources disposed such that light from each of the individual light sources passes through an optical element having optical power, reflects off of a reference or test object, passes through the optical element, and is received by a detector, wherein light from the Helmholtz source is used to determine geometric and/or optical information of at least a portion of a surface of the reference or test object. In general, it is a characteristic of Helmholtz sources that the signal at the detector is independent of the relative position of the test or reference object relative to the Helmholtz source. As used herein, the term "optical element" means an element that refracts, reflects, and/or diffracts light and has either positive or negative optical power.

In such embodiments, the Helmholtz light source 130 is located at optical infinity with respect to eye 101. The Helmholtz principle includes the use of such infinite sources in combination with a telecentric detector system: i.e., a system that places the detector array at optical infinity with respect to the surface under measurement, in addition to insuring that the principal measured ray leaving the surface is parallel to the optical axis of the instrument. The Helmholtz corneal measurement principle has the Helmholtz light source at optical infinity and the telecentric observing system so that detector array 141 is also optically at an infinite distance from the images of the sources formed by the cornea. Such a measurement system is insensitive to axial misalignment of the corneal surface with respect to the instrument.

In one embodiment, the Helmholtz light source 130 comprises a second light source 132 which may comprise a plurality of lamps, such as LEDs or optical fiber tips. In one embodiment, second light source 132 comprises an LED and a plate 133 with plurality of holes or apertures in a surface that are illuminated by one or more backlight lamps with an optical element 131, which may comprise diffusers.

In one embodiment, lamps of second light sources 132 are located off the central optical axis 102 of assembly 100, and light from second light sources 132 is directed toward optical element 171 by third beamsplitter 176.

The operation of the topographer portion of system 100 may be conducted with the combined use of first light source 120 and the Helmholz light source 130. In operation, detector array 141 detects the light spots projected thereon from both Helmholz light source 130 (detected at a central portion of detector array 141) and first light sources 120 (detected at a peripheral portion of detector array 141) and provides corresponding output signals to processor. In general, the images of first light sources 120 that appear on detector array 141 emanate from an outer region of the surface of the cornea, and the images of Helmholz light source 130 that appear on detector array 141 emanate from a central or paraxial region of the surface of the cornea. Accordingly, even though information about the central region of the corneal surface (e.g., surface curvature) cannot be determined from the images of first light sources 120 on detector array 141, such information can be determined from the images of Helmholz light source 130 on detector array 141. A processor of controller 60 determines the locations and/or shapes of the light spots on detector array 141, and compares these locations and/or shapes to those expected based for a standard or model cornea, thereby allowing the processor to determine the corneal topography of eye 101. Accordingly, the topography of the entire corneal surface can be characterized by system 100 without a "hole" or missing data from the central corneal region.

A fourth light source 201 off the central axis 102 may be directed along optical axis 102 by mirrors 177, 179 disposed on or near the aperture 178, perpendicular to the optical axis 102 are configured as a pupil retroreflection illuminator. The pupil retroreflecton illuminator is configured to direct a disc of light toward patient's eye 101, whereby the disc of light may be reflected from reflective surfaces within eye 101, and the reflected light is transmitted by optical path 170 to detector 141. The pupil retroreflection illuminators may optionally be configured such that, when the patient's pupil is dilated, the disc of light from light source 201 is reflected from an implanted IOL to image the IOL, including any fiducial marks; if IOL is imperfectly placed, detector 141 may be used to determine IOL edges are decentered. Also, images from detector 141 using the pupil retroreflection illuminator may see folds, for instance, unfolded edge if the IOL did not unfold properly.

Wavefront aberrometer subsystem 150 of assembly 100 comprises a third light source 152 providing a probe beam and a wavefront sensor 155. Wavefront aberrometer subsystem 150 preferably further comprises a collimating lens 154, a polarizing beamsplitter 156, an adjustable telescope comprising a first optical element, lens 163 and a second optical element, lens 164, a movable stage or platform 166, and a dynamic-range limiting aperture 165 for limiting a dynamic range of light provided to wavefront sensor 155 so as to preclude data ambiguity. Light from the wavefront aberrometer subsystem is directed to one of the constituent optical elements of the optical system 170 disposed along a central axis 102 passing through the opening or aperture 114 of the structure 110. It will be appreciated by those of skill in the art that the lenses 163, 164, or any of the other lenses discussed herein, may be replaced or supplemented by another type of converging or diverging optical element, such as a diffractive optical element.

Light source 152 may be an 840 nm SLD (super luminescent laser diode). An SLD is similar to a laser in that the light originates from a very small emitter area. However, unlike a laser, the spectral width of the SLD is very broad, about 40 nm. This tends to reduce speckle effects and improve the images that are used for wavefront measurements.

Beneficially, wavefront sensor 155 may be a Shack-Hartmann wavefront sensor comprising a detector array and a plurality of lenslets for focusing received light onto its detector array. In that case, the detector array may be a CCD, a CMOS array, or another electronic photosensitive device. However, other wavefront sensors may be employed instead. Embodiments of wavefront sensors which may be employed in one or more systems described herein are described in U.S. Pat. No. 6,550,917, issued to Neal et al. on Apr. 22, 2003, and U.S. Pat. No. 5,777,719, issued to Williams et al. on Jul. 7, 1998, both of which patents are hereby incorporated herein by reference in their entirety.

The aperture or opening in the middle of the group of first light sources 120 (e.g., aperture 114 in principal surface 112 of structure 110) allows assembly 100 to provide a probe beam into eye 101 to characterize its total ocular aberrations. Accordingly, third light source 152 supplies a probe beam through a light source polarizing beam splitter 156 and polarizing beam splitter 162 to first beamsplitter 172 of optical system 170. First beamsplitter 172 directs the probe beam through aperture 114 to eye 101. Preferably, light from the probe beam is scattered from the retina of eye 100, and at least a portion of the scattered light passes back through aperture 114 to first beamsplitter 172. First beamsplitter 172 directs the back scattered light back through beam splitter 172 to polarizing beamsplitter 162, mirror 153 to wavefront sensor 155.

Wavefront sensor 155 outputs signals to a processor of controller 60 which uses the signals to determine ocular aberrations of eye 101. Preferably, the processor is able to better characterize eye 101 by considering the corneal topography of eye 101 measured by corneal topography subsystem 140, which may also be determined by the processor based on outputs of detector array 141, as explained above.

In operation of wavefront aberrometer subsystem 150, light from light source 152 is collimated by lens 154. The light passes through light source polarizing beam splitter 156. The light entering light source polarizing beam splitter 156 is partially polarized. Light source polarizing beam splitter 156 reflects light having a first, S, polarization, and transmits light having a second, P, polarization so the exiting light is 100% linearly polarized. In this case, S and P refer to polarization directions relative to the hypotenuse in light source polarizing beam splitter 156.

Light from light source polarizing beam splitter 156 enters polarizing beamsplitter 162. The hypotenuse of polarizing beamsplitter 162 is rotated 90 degrees relative to the hypotenuse of light source polarizing beamsplitter 156 so the light is now S polarized relative the hypotenuse of polarizing beamsplitter 162 and therefore the light reflects upwards. The light from polarizing beamsplitter 162 travels upward and passes through toward beam splitter 172, retaining its S polarization, and then travels through quarter wave plate 171. Quarter wave plate 171 converts the light to circular polarization. The light then travels through aperture 114 in principal surface 112 of structure 110 to eye 101. Preferably, the beam diameter on the cornea is between 1 and 2 mm. Then the light travels through the cornea and focuses onto the retina of eye 101.

The focused spot of light becomes a light source that is used to characterize eye 101 with wavefront sensor 155.

Light from the probe beam that impinges on the retina of eye 101 scatters in various directions. Some of the light reflects back as a semi-collimated beam back towards assembly 100. Upon scattering, about 90% of the light retains its polarization. So the light traveling back towards assembly is substantially still circularly polarized. The light then travels through aperture 114 in principal surface 112 of structure 110, through quarterwave plate 171, and is converted back to linear polarization. Quarterwave plate 171 converts the polarization of the light from the eye's retina so that it is P polarized, in contrast to probe beam received from third light source 150 having the S polarization. This P polarized light then reflects off of first beamsplitter 172, and then reaches polarizing beamsplitter 162. Since the light is now P polarized relative the hypotenuse of polarizing beamsplitter 162, the beam is transmitted and then continues onto mirror 153. After being reflected by mirror 153, light is sent to an adjustable telescope comprising a first optical element 164 and a second optical element (e.g., lens) 163 and a movable stage or platform 166. The beam is also directed through a dynamic-range limiting aperture 165 for limiting a dynamic range of light provided to wavefront sensor 155 so as to preclude data ambiguity.

When wavefront sensor 155 is a Shack-Hartmann sensor, the light is collected by the lenslet array in wavefront sensor 155 and an image of spots appears on the detector array (e.g., CCD) in wavefront sensor 155. This image is then provided to a processor of controller 60 and analyzed to compute the refraction and aberrations of eye 101.

OCT subsystem 190 of assembly 100 may comprise an OCT assembly 191, and a third optical path 192 which directs the OCT beam of the OCT light source to the first optical path 170. The third optical path 192 may comprise a fiber optic line 196, for conducting the OCT beam from the OCT light source of OCT assembly 191, a Z-scan device 193 operable to alter the focus of the beam in the Z-direction (i.e., along the direction of propagation of the OCT beam) under control of the controller, and X-scan device 195, and a Y-scan device 197 operable to translate the OCT beam in the X and Y directions (i.e., perpendicular to the direction of propagation of the of the OCT beam), respectively, under control of controller 60. The OCT light source and reference arm may be incorporated into assembly 100 of optical measurement system 1 shown in FIG. 5A. Alternatively, OCT assembly 191 may be housed in a second unit or housing 200 and the OCT beam from the OCT source may be directed from second unit 200 to the main unit by optical pathway 192.

Beneficially, the OCT systems and methods employed in optical measurement system 1 and assembly 100 may employ swept source optical coherence tomography (SS-OCT) as described above. Beneficially, optical measurement system 1, assembly 100 and OCT subsystem may each comprise OCT interferometer 1000.

As explained above, in SS-OCT, a rapid-scanning laser source is employed. By rapidly sweeping the source wavelength over a broad wavelength range, and collecting all the scattering and reflection information at each wavelength and at each position, the collected spectral data may be inverse Fourier transformed to recover the spatial depth-dependent information for the object under test (e.g., eye 101).

Figure 6:
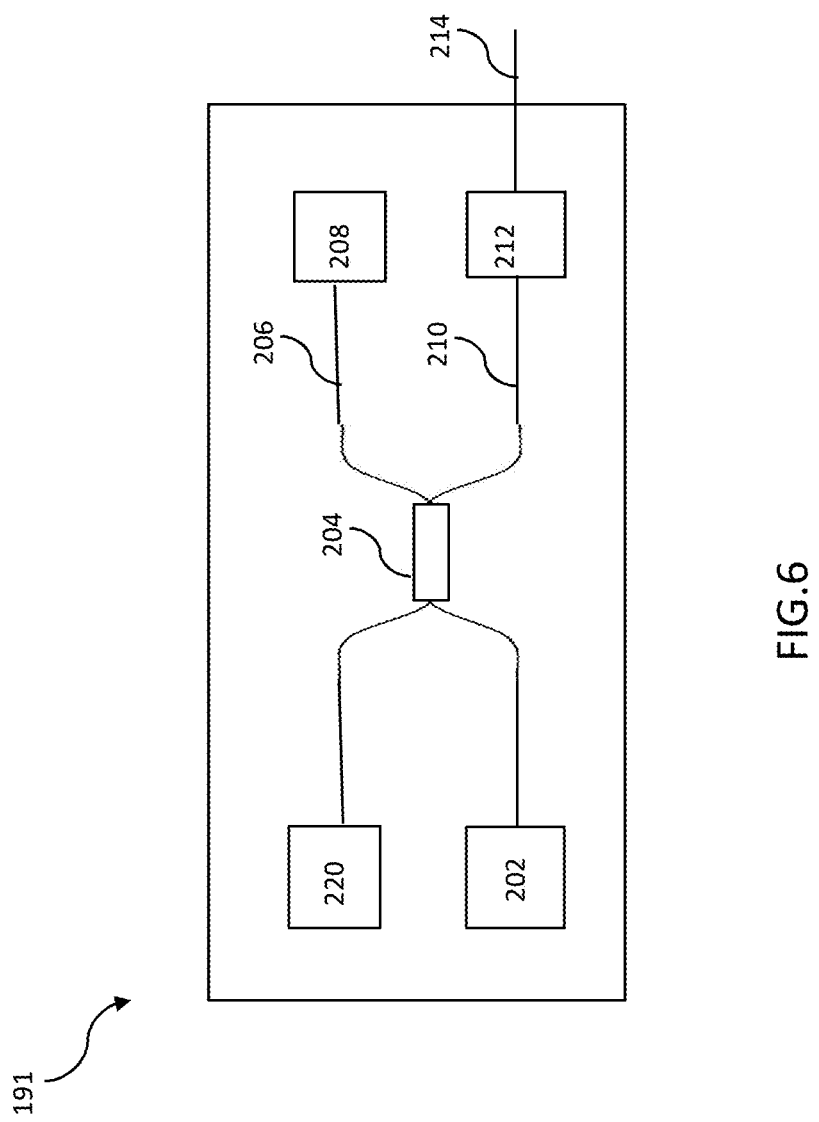
FIG. 6 is a block diagram of an OCT assembly according to many embodiments of the present invention.

As shown in FIG. 6, OCT assembly 191 of OCT subsystem 190 includes a swept light source 202 that is split by a coupler 204 into a reference arm 206 and a sample arm 210. The reference arm 206 includes a module 208 containing a reference reflection along with suitable dispersion and path length compensation as described above. In particular, reference arm 206 may include two different types of optical fibers (e.g., an HI-1060 type optical fiber and a SM-980 type optical fiber) arranged in series to compensate for the phase dispersion in sample arm 210. These two optical fibers having different dispersion coefficients can be balanced by selecting corresponding lengths for the optical fibers to improve the resolution of the OCT peaks in the OCT signal. Sample arm 210 of OCT assembly 191 has an output connector 212 that serves as an interface to the rest of optical measurement system 1. The return signals from both the reference and sample arms 206, 210 are then directed by coupler 204 to a detection device 220. In FIG. 6, a swept source technique may be used with a laser wavelength of 1060 nm swept over a range of 8-50 mm depth.

Figure 7:
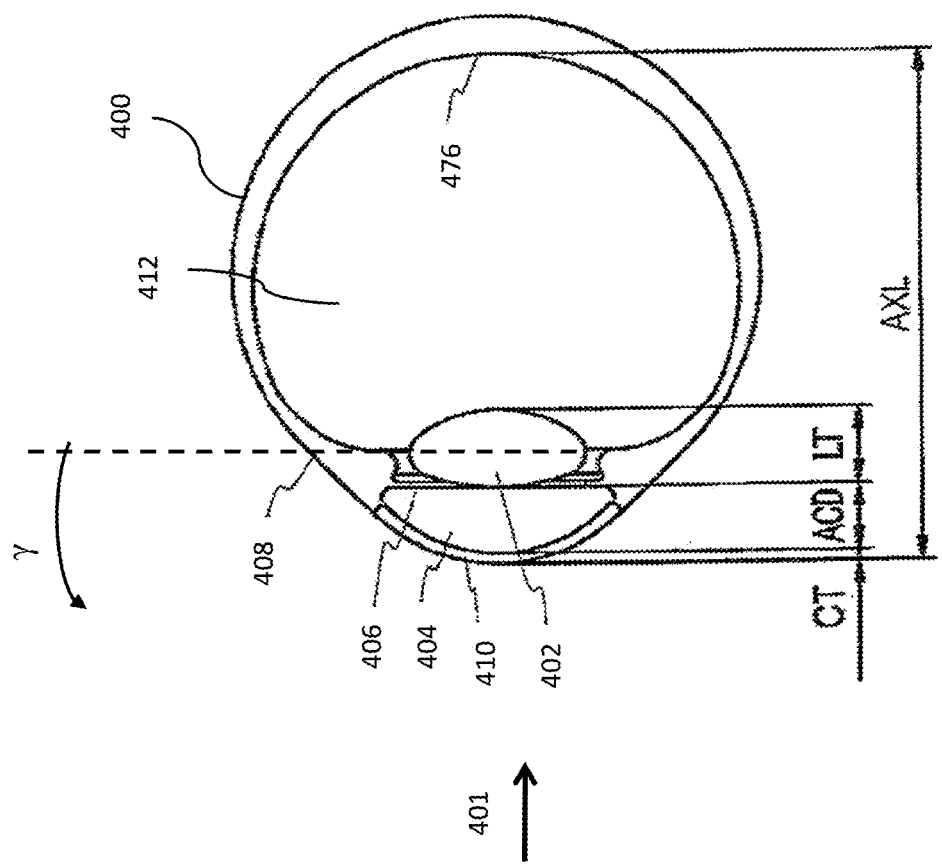
FIG. 7 is a schematic drawing of a human eye.

FIG. 7 is a schematic drawing of a human eye 400. In many embodiments, a light beam 401 from a light source enters the eye from the left of FIG. 7, refracts into the cornea 410, passes through the anterior chamber 404, the iris 406 through the pupil, and reaches lens 402. After refracting into the lens, light passes through the vitreous chamber 412, and strikes the retina 476, which detects the light and converts it to an electric signal transmitted through the optic nerve to the brain (not shown). The vitreous chamber 412 contains the vitreous humor, a clear liquid disposed between the lens 402 and retina 476. As indicated in FIG. 7, cornea 410 has corneal thickness (CT), here considered as the distance between the anterior and posterior surfaces of the cornea. Anterior chamber 404 has anterior chamber depth (ACD), which is the distance between the anterior surface of the cornea and the anterior surface of the lens. Lens 402 has lens thickness (LT) which is the distance between the anterior and posterior surfaces of the lens. The eye has an axial length (AXL) which is the distance between the anterior surface of the cornea and the retina 476. FIG. 7 also illustrates that, in many subjects the lens, including the lens capsule, may be tilted at one or more angles relative to the optical axis, including an angle γ relative to the optical axis of the eye.

The optical system may also be arranged so that the movement pattern of the scan mirrors provides a lateral motion across the retina so that the shape of the retina may be determined. It is of particular interest to measure the shape and location of the depressed region of the retina named the foveal pit. When the patient is looking directly into the instrument, with their line of sight aligned to the fixation target, the foveal pit will be in center of the OCT lateral scan. This information is beneficial in that it informs the instrument operator if the patient was looking directly at the target when the measurement was made. Retinal scans are also useful in detecting disease conditions. In some cases there may be an absence of a foveal pit that also is considered an indication of a corneal abnormality.

The average axial length of the adult human eye is about 24 mm Since the full range imaging depth of the OCT measurements are only about 5 mm to 8 mm, then OCT scanning may provide for OCT scans at different depths of the eye that can be combined together to form a combined OCT image of the eye. The OCT measurements may include OCT imaging at various depths of the patient's eye for imaging: (1) at least a portion of the retina, (2) at least a portion of the anterior portion of the eye, including at least a portion of the cornea (anterior and posterior), iris, and lens (anterior and posterior), and (3) performing axial eye length measurements.

FIGS. 8A-8C illustrate various aspects of OCT subsystem 190. FIG. 8A illustrates a preferred scanning region for OCT subsystem 190 according to many embodiments. The scanning region may be defined from starting point 301 to ending point 302 at the anterior portion of the eye extending in a direction transverse the direction of propagation of the OCT beam and also extending in a direction parallel to an axis defining the axial length of the eye to the posterior portion 304 of the eye. The lateral scanning region should generally be sufficiently large in the lateral direction to permit imaging of the central portion of the cornea, at least a portion of the iris, at least a portion of the lens and at least of the retina. It should be noted that a region 303 between the posterior portion of the lens and the surface of the retina may optionally not be scanned by OCT subsystem 190 because the portion 330 does not contain anatomical structure for 3D analysis.

FIG. 8B shows a representative graph of an intensity of an OCT signal of OCT subsystem 190 according to many embodiments as a function of depth along the axis defining the axial length of the eye. The graph generally exhibits approximately four peaks having a complex structure: (1) a peak 310 having a doublet-like structure and generally corresponding to a location of the cornea; (2) a peak 320 having a doublet-like structure and generally corresponding to a location of an anterior surface of the lens; (3) a peak 330 having a complex structure generally corresponding to a location of a posterior surface of the lens; and (4) a peak 340 generally corresponding to a location of a retina. A distance between peak 310 and peak 340 can be used to calculate the axial length (AL) of the eye. An OCT scan by OCT subsystem 190, including both an A-scan and B-scan, may be conducted for at least one location in the anterior portion of the eye (e.g., a location of a cornea, a location of an anterior surface of a lens and/or a location of a posterior surface of the lens) and at least one location in the posterior portion of the eye (e.g., at a location of a retina). In some embodiments, an OCT scan by OCT subsystem 190, including both an A-Scan and a B-scan is performed at a location corresponding to each of a location of the cornea, a location of an anterior surface of the lens, a location of a posterior surface of the lens, and a location corresponding to a retina.

It should be noted that because OCT subsystem 190 provides for the detection of various structures of the eye, including a location of the cornea, OCT subsystem 190 may be used as a ranging system to precisely align the patient in relation to optical measurement system 1. The use of OCT in a ranging system can significantly improve accuracy of corneal topography measurements, including keratometry measurements, which are sensitive to misalignment of the corneal structures.

FIG. 8C shows a cross-section of an eye obtained by an optical measurement system using an OCT subsystem such as OCT subsystem 190, which may employ an OCT interferometer such as OCT interferometer 1000.

Figure 9:
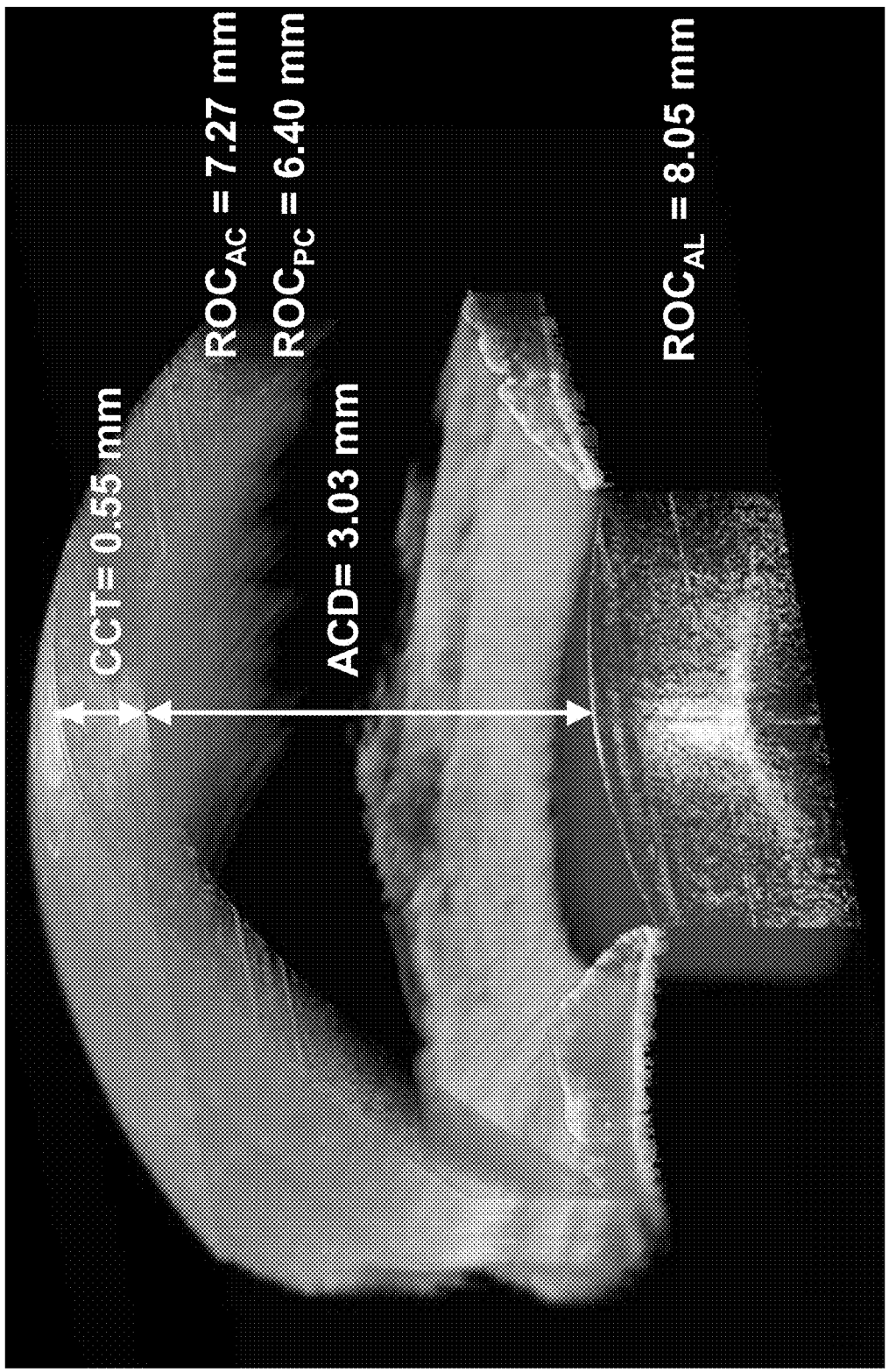
FIG. 9 is a 3-dimensional representation of an anterior portion of an eye obtained using the optical measurement system according to many embodiments.
Figure 10:
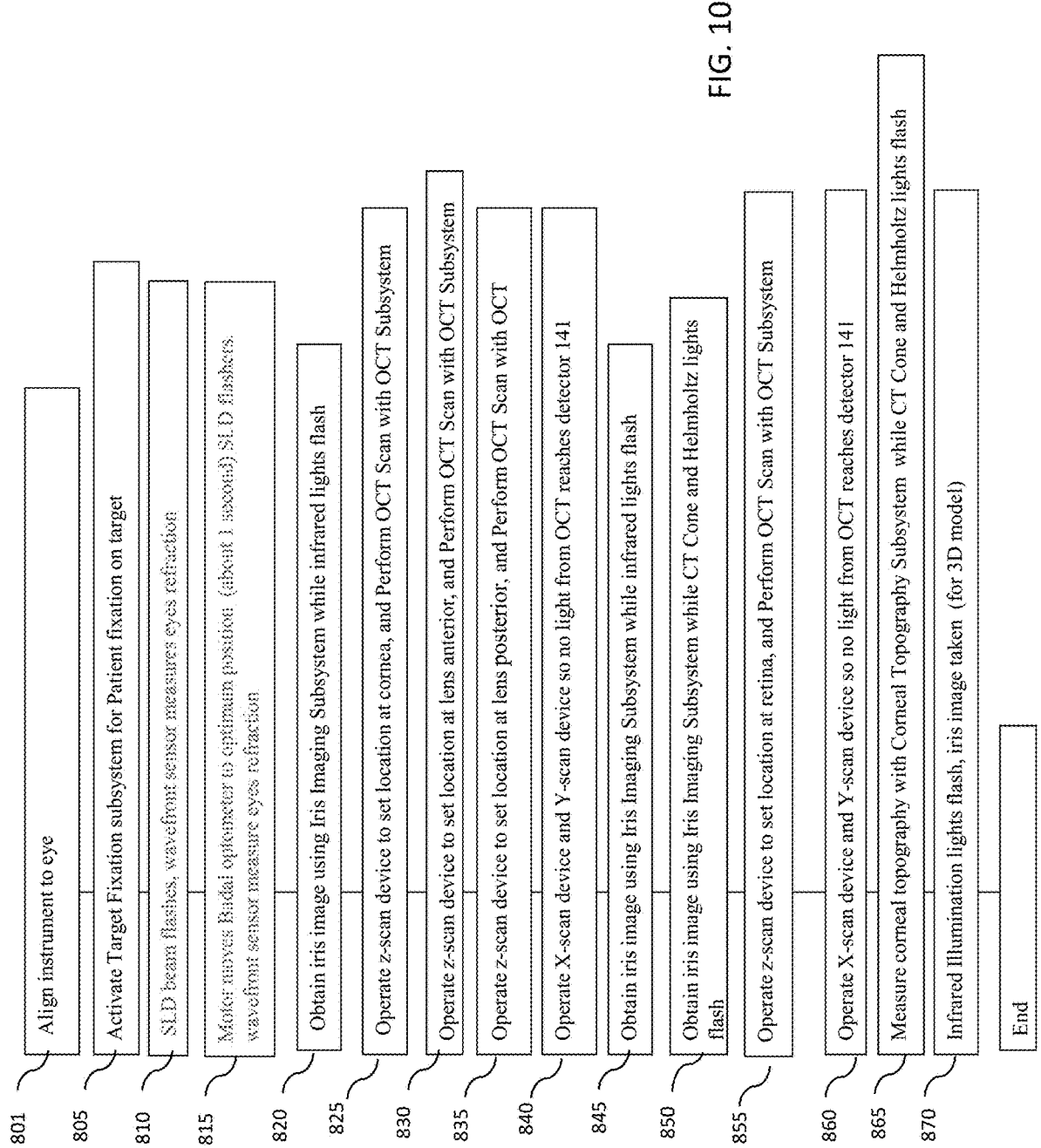
FIG. 10 is a flowchart of an example embodiment of a method for measuring one or more characteristics of an eye, including wavefront aberrometry, corneal topography and OCT measurements at various locations with the eye along the axial length of the eye.

FIG. 9 shows a 3 dimensional view of an eye obtained by an optical measurement system 1 using an OCT subsystem such as OCT subsystem 190. FIG. 9 evidences that the OCT subsystem is operable to obtain biometry measurements, including the central corneal thickness (CCT), the anterior chamber depth (ACD), the radius of curvature of the anterior cornea ($ROC_{AC}$), the radius of curvature of the Posterior cornea ($ROC_{PC}$) and the Radius of curvature of the axial length ($ROC_{AL}$).

OCT subsystem 190 may provide sufficiently resolved structural information to a structural assessment that may provide a user with an indication of suitability of a particular patient for a laser cataract procedure. In one embodiment, an OCT scan performed by OCT subsystem 190 at or near the retina (i.e., a retina scan) is sufficiently resolved to identify the foveal pit location and depth, wherein a lack of depression indicates an unhealthy retina.

In another embodiment, optical measurement system 1 provides one or more measurements sufficient to provide an assessment of the tear film of a patient. In one embodiment, the tear film assessment comprises a comparison of a wavefront aberrometry map and a corneal topography map or OCT map of the patient's eye, by, for instance, subtracting the corneal topography map from the wavefront aberrometry map, to obtain a difference map. A determination of whether the tear film is broken (if not smooth); an assessment of the tear film, including tear film breakup, can be obtained by reviewing the shape of spots on the topographer. For instance, a finding or indication that the tear film is disrupted, or broken, may be based upon the shape of a spot in that, if the spots are not round, and have, for instance, an oblong or broken up shape, it indicates that tear film is disrupted. The existence of such a disrupted tear film may indicate that K value, and other ocular measurements may not be reliable In operation, as shown in FIG. 5A, after exiting connector 212, an OCT probe beam 214 may be collimated, for example using a collimating optical fiber 196. Following collimating fiber 196 OCT probe beam 214 is directed to Z-scan device 193 operable to change the focal point of OCT probe beam 214 in the Z-direction, and X- and Y-scan devices 195 and 197, which are operable to scan the OCT beam in X and Y-directions perpendicular to the Z-direction.

Following the collimating optical fiber 196, OCT probe beam 214 continues through a Z-scan device 193. Z-scan device 193 may comprise a Z-telescope 194 which is operable to scan focus position of OCT probe beam 214 in the patient's eye 101 along the Z axis. For example, Z-telescope 194 may include a Galilean telescope with two lens groups (each lens group includes one or more lenses). One of the lens groups moves along the Z axis about the collimation position of Z-scan device 193. In this way, the focus position in the patient's eye 101 moves along the Z axis. In general, there is a relationship between the motion of lens group and the motion of the focus point. The exact relationship between the motion of the lens and the motion of the focus in the Z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. Z-telescope 194 functions as a Z-scan device for changing the focus point of OCT probe beam 214 in patient's eye 101. Z-scan telescope 194 can be controlled automatically and dynamically by controller 60 and selected to be independent or to interplay with X and Y scan devices 195 and 197.

After passing through the z-scan device, the OCT probe beam 214 is incident upon an X-scan device 195, which is operable to scan the OCT probe beam 214 in the X direction, which is dominantly transverse to the Z axis and transverse to the direction of propagation of OCT probe beam 214. X-scan device 195 is controlled by controller 60, and can include suitable components, such as a lens coupled to a MEMS device, a motor, galvanometer, or any other well-known optic moving device. The relationship of the motion of OCT probe beam 214 as a function of the motion of the actuator of X-scan device 195 does not have to be fixed or linear. Modeling or calibrated measurement of the relationship or a combination of both can be determined and used to direct the location of OCT probe beam 214.

After being directed by the X-scan device 195, OCT probe beam 214 is incident upon a Y scan device 197, which is operable to scan OCT probe beam 214 in the Y direction, which is dominantly transverse to the X and Z axes. Y-scan device 197 is controlled by the controller 60, and can include suitable components, such as a lens coupled to a MEMS device, motor, galvanometer, or any other well-known optic moving device. The relationship of the motion of the beam as a function of the motion of the Y actuator of Y-scan device 197 does not have to be fixed or linear. Modeling or calibrated measurement of the relationship or a combination of both can be determined and used to direct the location of OCT probe beam 214. Alternatively, the functionality of X-Scan device 195 and Y-Scan device 197 can be provided by an XY-scan device configured to scan OCT probe beam 214 in two dimensions transverse to the Z axis and the propagation direction of OCT probe beam 214. The X-scan and Y scan devices 195, 197 change the resulting direction of OCT probe beam 214, causing lateral displacements of OCT probe beam 214 located in the patient's eye 101.

OCT probe beam 214 is then directed to beam splitter 173 through lens 175 through quarter wave plate 171 and aperture 114 and to the patient eye 101. Reflections and scattering off of structures within the eye provide return beams that retrace back through the patient interface quarter wave plate 171, lens 175, beam splitter 173, Y-scan device 197, X-scan device 195, Z-scan device 193, optical fiber 196 and beam combiner 204 (FIG. 6), and back into the OCT detection device 220. The returning back reflections of the sample arm 201 are combined with the returning reference portion 206 and directed into the detector portion of the OCT detection device 220, which generates OCT signals in response to the combined returning beams. The generated OCT signals that are in turn interpreted by controller 60 to determine the spatial disposition of the structures of interest in patient's eye 101. The generated OCT signals can also be interpreted by the controller to determine the spatial disposition of the structures of interest in the patient's eye 101. The generated OCT signals can also be interpreted by the control electronics to align the position and orientation of the patient eye within the patient interface.

Optical measurement systems disclosed herein may comprise an iris imaging subsystem 40. Iris imaging subsystem 40 generally may comprise an infrared light source, for example an infrared light source 152, and detector 141. In operation light from light source 152 is directed along second optical path 160 to first optical path 170 and is subsequently directed to eye 101 as described above. Light reflected from the iris of eye 101 is reflected back along first optical path 170 to detector 141. In normal use, an operator will adjust a position or alignment of system 100 in XY and Z directions to align the patient according to the image detector array 141. In one embodiment of the iris imaging subsystem, eye 101 is illuminated with infrared light from light source 152. In this way, the wavefront obtained by wavefront sensor 155 will be registered to the image from detector array 141.

The image that the operator sees is the iris of eye 100. The cornea generally magnifies and slightly displaces the image from the physical location of the iris. So the alignment that is done is actually to the entrance pupil of the eye. This is generally the desired condition for wavefront sensing and iris registration.

Iris images obtained by the iris imaging subsystem may be used for registering and/or fusing the multiple data sets obtained by the various subsystems of optical measurement system 1 by methods described, for instance, in "Method for registering multiple data sets," U.S. patent application Ser. No. 12/418,841, which is incorporated herein by reference. As set forth in application Ser. No. 12/418,841, wavefront aberrometry may be fused with corneal topography, optical coherence tomography and wavefront, optical coherence tomography and topography, pachymetry and wavefront, etc. For instance, with image recognition techniques it is possible to find the position and extent of various features in an image. Regarding iris registration images, features that are available include the position, size and shape of the pupil, the position, size and shape of the outer iris boundary (OIB), salient iris features (landmarks) and other features as are determined to be needed. Using these techniques, patient movement between measurements (and/or during a measurement sequence) can be identified, as well as changes in the eye itself (including those induced by the measurement, such as changes in the size of the pupil, changes in pupil location, etc.).

In many embodiments, optical measurement system 1 includes a target fixation subsystem 50 (FIG. 4), and assembly 100 shown in FIGS. 5A and 5B includes fixation target subsystem 180 which includes a fixation target 182 for the patient to view. Fixation target subsystem 180 is used to control the patient's accommodation, because it is often desired to measure the refraction and wavefront aberrations when eye 100 is focused at its far point (e.g., because LASIK treatments are primarily based on this). In the target fixation subsystem, a projection of a target, for instance a cross-hair pattern is projected onto the eye of the patient, the cross hair pattern being formed by a backlit LED and a film.

In operation, light originates from the light source 152 or, alternatively, from video target backlight 182 and lens 186. Lens 185 collects the light and forms an aerial image T2. This aerial image is the one that the patient views. The patient focus is maintained on aerial image 182 during measurement so as to maintain the eye in a fixed focal position.

The operating sequence the optical measurement system and methods of the present is not particularly limited. A scan of the patient's eye may comprise one or more of a wavefront aberrometry measurement of a patient's eye utilizing the wavefront aberrometry subsystem, a corneal topography measurement of a patient's eye and an OCT scan of the patient's eye using the OCT subsystem, wherein the OCT scan includes a scan at each or one or more locations within the eye of the patient. These locations of the OCT scan may correspond to the location of the cornea, the location of the anterior portion of the lens, the location of the posterior portion of the lens and the location of the retina. In a preferred embodiment, the operating sequence includes each of a wavefront aberrometry measurement, a corneal topography measurement and an OCT scan, wherein the OCT scan measures at least the locations of the retina, the cornea and one of anterior portion of the patient's lens. An iris image may be taken simultaneously with or sequentially with each of the measurements taken with wavefront aberrometry subsystem, the corneal topography subsystem and the OCT subsystem, including an iris image take simultaneously with or sequentially with the location of each OCT scan. This results in improved accuracy in the 3-dimensional modeling of the patient's eye by permitting the various data sets to be fused and merged into a 3-dimensional model.

Optical measurement system 1 and the optical measurements obtained therewith may be used pre-operatively, i.e. before a cataract surgery or other surgical procedure, for, e.g., eye biometry and other measurements, diagnostics and surgical planning Surgical planning may include one or more predictive models. In the one or more predictive models, one or more characteristics of the postoperative condition of the patient's eye or vision is modeled based on one or more selected from the group consisting of preoperative measurements obtained from the optical measurement system 1, a contemplated surgical intervention, and on or more algorithms or models stored in the memory of the optical measurement system 1 and executed by the processor. The contemplated surgical intervention may include the selection of an IOL for placement, the selection of an IOL characteristic, the nature or type of incision to be used during surgery (e.g., relaxation incision), or one or more post-operative vision characteristics requested by the patient.

Optical measurement system 1 and the optical measurements obtained therewith may be used intra-operatively, i.e., during a cataract surgery or other surgical procedure, for, e.g., intraoperative eye diagnostics, determining IOL placement and position, surgical planning, and control/or of a laser surgical system. For instance, in the case of laser cataract surgical procedure, any measurement data obtained preoperatively by the optical measurement instrument may be transferred to a memory associated with a cataract laser surgical system for use before, during or after either the placement of a capsulotomy, fragmentation or a patient's lens or IOL placement during the cataract surgery. In some embodiments, measurements using optical measurement system 1 may be taken during the surgical procedure to determine whether the IOL is properly placed in the patient's eye. In this regard, conditions measured during the surgical procedure may be compared to a predicted condition of the patient's eye based on pre-operative measurements, and a difference between the predicted condition and the actual measured condition may be used to undertake additional or corrective actions during the cataract surgery or other surgical procedure.

Optical measurement system 1 and the optical measurements obtained therewith may be used postoperatively, i.e., after a cataract surgery or other surgical procedure, for, e.g., post-operative measurement, postoperative eye diagnostics, postoperative IOL placement and position determinations, and corrective treatment planning if necessary. The postoperative testing may occur sufficiently after the surgery that the patient's eye has had sufficient time to heal and the patient's vision has achieved a stable, postsurgical state. A postoperative condition may be compared to one or more predicted condition performed pre-operatively, and a difference between the preoperatively predicted condition and the postoperatively measured condition may be used to plan additional or corrective actions during the cataract surgery or other surgical procedure.

Optical measurement system 1, including the corneal topography subsystem, the OCT subsystem and the wavefront aberrometry subsystem, utilizing a suitable operating sequence as disclosed herein, is operable to measure one, more than one or all of the following: ocular biometry information, anterior corneal surface information, posterior corneal surface information, anterior lens surface information, posterior lens surface information, lens tilt information and lens position information. In some embodiments, the ocular biometry information may include a plurality of central corneal thicknesses (CCT), an anterior chamber depth (ACT), a pupil diameter (PD), a white to white distance (WTW), a lens thickness (LT), an axial length (AL) and a retinal layer thickness. This measurement data may be stored in memory 62 associated with controller 60. The plurality of characteristics may be measured preoperatively, and where appropriate, intra-operatively, and postoperatively.

In some embodiments, memory 62 associated with controller 60 may store intraocular lens (IOL) model data for a plurality of IOL models, each of the IOL models having associated with it a plurality of predetermined parameters selected from the group consisting of dioptic power, refractive index, asphericity, toricity, haptic angulation and lens filter. The IOL data may be used by one or more processors of optical measurement system 1, in conjunction with measurement data of a subject's eye obtained by optical measurement system 1, for cataract diagnostics or cataract treatment planning, which may include specifying and/or selecting a particular IOL for a subject's eye. For example, one or more processors of optical measurement system 1 may execute an algorithm which includes: accessing the plurality of IOL models stored in, and for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL for the subject's eye from the plurality of IOL models corresponding to the optimized IOL based on a predetermined criteria.

In some embodiments, one or more processors of optical measurement system 1 may execute an algorithm comprising: determining a desired postoperative condition of the subject's eye; empirically calculating a post-operative condition of the eye based at least partially on the measured eye characteristics; and predictively estimating, in accordance with an output of said empirically calculating and the eye characteristics, at least one parameter of an intraocular lens for implantation into the subject's eye to obtain the desired postoperative condition.

In many embodiments, the eye imaging and diagnostic system further comprises a memory operable to store Intraocular Lens ("IOL") Data, the IOL data including a plurality of dioptic power, anterior and posterior radius, IOL thickness, refractive index, asphericity, toricity, echelette features, haptic angulation and lens filter.

In many embodiments, the eye imaging and diagnostic system further comprises a memory operable to store intraocular lens ("IOL") model data for a plurality of IOL models, IOL model having associated with a plurality of predetermined parameters selected from the group consisting of dioptic power, anterior and posterior radius, IOL thickness, refractive index, asphericity, toricity, echelette features, haptic angulation and lens filter.

An improved system for selecting an intraocular lens (IOL) for implantation, comprises: a memory operable to store data acquired from each of the corneal topography subsystem, the wavefront sensor subsystem and the Optical Coherence Tomography subsystem, wherein the stored data includes a plurality of ocular biometry information, anterior corneal surface information, posterior corneal surface information, anterior lens surface information, and posterior lens surface information, lens tilt information and lens position information; the memory further operable to store intraocular lens ("IOL") model data for a plurality of IOL models, IOL model having associated with it a plurality of predetermined parameters selected from the group consisting of dioptic power, anterior and posterior radius, IOL thickness, refractive index, asphericity, toricity, echelette features, haptic angulation and lens filter; and a processor coupled to the memory, the processor deriving the treatment of the eye of the patient applying, for each of the plurality of identified IOL Model, to: (1) predict a position of one of the identified IOL Models when implanted in the subject eye, based on the plurality of characteristics; (2) simulate the subject eye based on the plurality of IOL predetermined parameters and the predicted IOL position; (3) perform one or more of ray tracing and a IOL spherical equivalent (SE) and cylinder (C) power calculation, as well as optionally, to determine the optimum IOL orientation based on said eye model; and (4) propose one IOL power for one or more IOL models from the plurality of IOLs corresponding to the optimized IOL(s) based on predetermined criteria; and (5) show the simulated optical quality and/or visual performance provided by each of the proposed IOL models for distance and/or for any other vergence.

A method of selecting an intraocular lens (IOL) to be implanted in a subject's eye, comprising: measuring a plurality of eye characteristics comprising ocular biometry information, anterior corneal surface information, posterior corneal surface information, anterior lens surface information, and posterior lens surface information, lens tilt information and lens position information; and for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation and lens filter: (1) modeling the subject eye with the intraocular lens; (2) simulating the subject eye based on the plurality of IOL predetermined parameters and the predicted IOL position; (3) performing a ray tracing and a IOL spherical equivalent (SE) and cylinder (C) power calculation, as well as determine the optimum IOL orientation based on said eye model; and (4) proposing one IOL power for one or more IOL models from the plurality of IOLs corresponding to the optimized IOL(s) based on predetermined criteria; and optionally (5) show the simulated optical quality and/or visual performance provided by each of the proposed IOL models for distance and/or for any other vergence.

A tangible computer-readable storage device storing computer instructions which, when read by a computer, cause the computer to perform a method comprising: receiving a plurality of eye characteristics comprising ocular biometry information, anterior corneal surface information, posterior corneal surface information, anterior lens surface information, and posterior lens surface information, lens tilt information and lens position information; for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation and lens filter: (1) simulating a geometry of the subject eye with each of the plurality of intraocular lenses (IOL) implanted, in accordance with the plurality of eye characteristics; (2) performing a ray tracing and a IOL spherical equivalent (SE) and cylinder (C) power calculation, as well as optionally determining the optimum IOL orientation based on said eye model; (3) proposing one IOL power for one or more IOL models from the plurality of IOLs corresponding to the optimized IOL(s) based on predetermined criteria; and optionally (4) showing the simulated optical quality and/or visual performance provided by each of the proposed IOL models for distance and/or for any other vergence.

A method of predicting the intraocular lens position comprising: determining a plurality of eye characteristics before cataract surgery, comprising ocular biometry information, anterior corneal surface information, posterior corneal surface information, anterior lens surface information, and posterior lens surface information, lens tilt information and lens position information; determining a plurality of eye characteristics after cataract surgery, comprising ocular biometry information, anterior corneal surface information, posterior corneal surface information, anterior lens surface information, and posterior lens surface information, lens tilt information and lens position information; calculating or measuring, based on a mathematical relationship, a distance from the apex to a plane of the intraocular lens after an ocular surgical procedure; calculating an optical power of the intraocular lens suitable for providing a predetermined refractive outcome; wherein a mathematical relationship is found between the preoperative and postoperative eye characteristics that accurately predict the measured distance from the apex to the plane where the intraocular lens is.

An improved system for planning a refractive treatment of an eye of a patient, the system comprising: a memory operable to store eye measurement data comprising ocular biometry information, anterior corneal surface information, posterior corneal surface information, anterior lens surface information, and posterior lens surface information, lens tilt information and lens position information; a processor coupled to the memory, the processor deriving the treatment of the eye of the patient applying an effective treatment transfer function, wherein the effective treatment transfer function is derived from, for each of a plurality of prior eye treatments, a correlation between a pre-treatment vector characterizing the eye measurement data before treatment, and a post-treatment vector characterizing post-treatment eye measurement data of the associated eye; an output coupled to the processor so as to transmit the treatment to facilitate improving refraction of the eye of the patient. The processor may comprise tangible media embodying machine readable instructions for implementing the derivation of the treatment.

An improved method for planning a refractive treatment of an eye of a patient, the system comprises: measuring a plurality of ocular biometry information, anterior corneal surface information, posterior corneal surface information, anterior lens surface information, and posterior lens surface information, lens tilt information and lens position information.

A method of customizing at least one parameter of an intraocular lens, comprising: measuring a plurality of eye characteristics comprising ocular biometry information, anterior corneal surface information, posterior corneal surface information, anterior lens surface information, and posterior lens surface information, lens tilt information and lens position information; determining a desired postoperative condition of the eye; empirically calculating a postoperative condition of the eye based at least partially on the measured eye characteristics; and predictively estimating, in accordance with an output of said empirically calculating and the eye characteristics, with at least one parameter of the intraocular lens to obtain the desired postoperative condition.

A method of adjusting the refractive power in an eye of a patient who has undergone cataract surgery comprising: measuring a plurality of post-operative eye characteristics in an eye of a patient who has previously undergone cataract surgery, the eye characteristics comprising ocular biometry information, anterior corneal surface information, posterior corneal surface information, anterior lens surface information, and posterior lens surface information, lens tilt information and lens position information; identifying a plurality of corrective procedure based at least partially on one of (1) a comparison of at least one measured pre-operative eye characteristic and the corresponding measured post-operative eye characteristic; and (2) a comparison of at least one predicted post-operative eye characteristic and the corresponding measured post-operative eye characteristic; for each of a plurality of corrective procedures: modeling the subject eye with the corrective procedure; modeling the subject eye based on the corrective procedure; performing one of a ray tracing and a power calculation based on said eye model; and selecting a corrective procedure from the plurality of IOL models corresponding to the optimized IOL based on a predetermined criteria.

In some embodiments, the system further comprises a processor configured to execute an algorithm. The algorithm comprises, for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL from the plurality of IOL models corresponding to the optimized IOL based on a predetermined criteria.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

All patents and patent applications cited here are hereby incorporated by reference hereby reference in their entirety.

The use of the terms "a" and "an" and "the" and similar referents in the context of describing the invention (especially in the context of the following claims) are to be construed to cover both the singular and the plural, unless otherwise indicated here or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values here are merely intended to serve as a shorthand method of referring individually to each separate value falling within the range, unless otherwise indicated herein, and each separate value is incorporated into the specification as if it were individually recited herein. All methods described here can be performed in any suitable order unless otherwise indicated here or otherwise clearly contradicted by context. The use of any and all examples, or exemplary language (e.g., "such as") provided herein, is intended merely to better illuminate embodiments of the invention, and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made and remain within the concept without departing from the spirit or scope of the invention. Such variations would become clear to one of ordinary skill in the art after inspection of the specification, drawings and claims herein. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

We claim:

1. A system, comprising:
    a swept laser light source configured to generate laser light having a frequency swept across a frequency bandwidth as a function of time;
    a sample path configured to direct a first portion of the laser light to an eye as a probe beam and to receive a returned portion of the probe beam from the eye, returned by at least one of reflection and scattering;
    a reference path for passing therethrough a second portion of the laser light, the reference path having a defined optical path length;
    a wavefront aberrometer;
    a corneal topographer;
    an iris imaging system;
    a structure having an aperture therethrough; and
    a detector configured to receive the returned portion of the probe beam from the eye and the second portion of the laser light from the swept laser light source which passed through the reference path, and in response thereto to output an optical coherence tomography (OCT) signal having peaks whose relative timing represents the depths of various reflection and scattered surfaces within the eye,
    wherein the reference path includes a first optical fiber of a first type having a first length, in series with a second optical fiber of a second type which is different than the first type and having a second length, wherein dispersion characteristics of the first optical fiber and the second optical fiber are significantly different than each other,
    wherein the sample path directs the probe beam to the eye through the aperture, and
    wherein all of the wavefront aberrometer, the corneal topographer, and the iris imaging system direct light to the eye through the aperture.

2. The system of claim 1, wherein the sample path includes a Z-axis telescope configured to focus the probe beam at a desired depth within the eye.

3. The system of claim 1, wherein the sample path includes a scanner configured to scan the probe beam in X and Y directions to span an X-Y OCT measurement space in the eye.

4. A system, comprising:
    a swept laser light source configured to generate laser light having a frequency swept across a frequency bandwidth as a function of time;
    a sample path configured to direct a first portion of the laser light to an eye as a probe beam and to receive a returned portion of the probe beam from the eye, returned by at least one of reflection and scattering;
    a reference path for passing therethrough a second portion of the laser light, the reference path having a defined optical path length; and
    a detector configured to receive the returned portion of the probe beam from the eye and the second portion of the laser light from the swept laser light source which passed through the reference path, and in response thereto to output an optical coherence tomography (OCT) signal having peaks whose relative timing represents the depths of various reflection and scattered surfaces within the eye, wherein the reference path includes a first optical fiber of a first type having a first length, in series with a second optical fiber of a second type which is different than the first type and having a second length, wherein dispersion characteristics of the first optical fiber and the second optical fiber are significantly different than each other, and a third optical fiber of a third type having a third length, in series with the first and second optical fibers, and wherein dispersion characteristics of the third optical fiber are significantly different than the dispersion characteristics of the first optical fiber and than the second optical fiber.

5. The system of claim 4, wherein the first optical fiber and the second optical fiber have substantially different group velocity dispersion constants than each other for at least one frequency within the bandwidth of the swept laser light source.

6. The system of claim 4, wherein a total group delay dispersion of a first portion of the laser light passing through the sample path and a total group delay dispersion of the second portion of the laser light passing through the reference path offset each other at the detector.

7. The system of claim 4, wherein the first optical fiber is an HI-1060 type optical fiber and the second optical fiber is an SM-980 type optical fiber.

8. The system of claim 4, wherein the first optical fiber, the second optical fiber and the third optical fiber all have substantially different group velocity dispersion constants than each other for at least one frequency within the bandwidth of the swept laser light source.

9. The system of claim 8, wherein a total group delay dispersion of a first portion of the laser light passing through the sample path and a total group delay dispersion of the second portion of the laser light passing through the reference path offset each other at the detector.

10. A method, comprising:
sweeping a frequency of a laser light source across a frequency bandwidth as a function of time to generate laser light whose frequency varies as a function of time;
directing a first portion of the laser light to an eye as a probe beam, and receiving a returned portion of the probe beam from the eye, returned by at least one of reflection and scattering via a sample path of an optical coherence tomography (OCT) interferometer;
passing a second portion of the laser light through a reference path of the OCT interferometer, the reference path having a defined optical path length; and
receiving at a detector the returned portion of the probe beam from the eye and the second portion of the laser light from the swept laser light source which passed through the reference path, and in response thereto outputting an OCT signal having peaks whose relative timing represents the depths of various reflection and scattered surfaces within the eye, wherein the reference path includes a first optical fiber of a first type having a first length, in series with a second optical fiber of a second type which is different than the first type and having a second length, and a third optical fiber of a third type having a third length, in series with the first and second optical fibers, wherein dispersion characteristics of the first optical fiber and the second optical fiber are significantly different than each other, and wherein dispersion characteristics of the third optical fiber are significantly different than the dispersion characteristics of the first optical fiber and than the second optical fiber.

11. The method of claim 10, wherein the first optical fiber and the second optical fiber have substantially different group velocity dispersion constants than each other for at least one frequency within the bandwidth of the swept laser light source.

12. The method of claim 10, wherein a total group delay dispersion of a first portion of the laser light passing through the sample path and a total group delay dispersion of the second portion of the laser light passing through the reference path offset each other at the detector.

13. The method of claim 10, wherein the first optical fiber is an HI-1060 type optical fiber and the second optical fiber is an SM-980 type optical fiber.

14. The method of claim 10, wherein the first optical fiber, the second optical fiber and the third optical fiber all have substantially different group velocity dispersion constants than each other for at least one frequency within the bandwidth of the swept laser light source.

15. The method of claim 14, wherein a total group delay dispersion of a first portion of the laser light passing through the sample path and a total group delay dispersion of the second portion of the laser light passing through the reference path offset each other at the detector.

16. The method of claim 10, further comprising focusing the probe beam at a desired depth within the eye via a Z-axis telescope.

17. The method of claim 10, scanning the probe beam in X and Y directions to span an X-Y OCT measurement space in the eye.

* * * * *